(12) United States Patent
Kragh

(10) Patent No.: US 9,280,684 B1
(45) Date of Patent: *Mar. 8, 2016

(54) IDENTITY VALIDATION AND VERIFICATION SYSTEM AND ASSOCIATED METHODS

(71) Applicant: James F. Kragh, Winter Park, FL (US)

(72) Inventor: James F. Kragh, Winter Park, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/613,115

(22) Filed: Feb. 3, 2015

Related U.S. Application Data

(63) Continuation-in-part of application No. 13/898,669, filed on May 21, 2013, now Pat. No. 8,984,282, which is a continuation-in-part of application No. 12/792,980, filed on Jun. 3, 2010, now Pat. No. 8,464,046.

(60) Provisional application No. 61/183,600, filed on Jun. 3, 2009.

(51) Int. Cl.
*G06F 21/00* (2013.01)
*G06F 21/62* (2013.01)
*G06F 17/30* (2006.01)

(52) U.S. Cl.
CPC ...... *G06F 21/6227* (2013.01); *G06F 17/30424* (2013.01)

(58) Field of Classification Search
USPC .......................................................... 713/156
See application file for complete search history.

(56) References Cited

U.S. PATENT DOCUMENTS

| | | | |
|---|---|---|---|
| 6,892,679 B2 | 5/2005 | Jameel et al. | |
| 7,047,204 B1 | 5/2006 | Wood et al. | |
| 7,078,647 B2 | 7/2006 | Kou et al. | |
| 7,239,285 B2 | 7/2007 | Cook | |
| 7,280,988 B2 | 10/2007 | Helsper et al. | |
| 7,424,437 B2 | 9/2008 | Maus et al. | |
| 7,668,734 B2 | 2/2010 | Pugh | |
| 7,742,982 B2 | 6/2010 | Chaudhuri et al. | |
| 2006/0206724 A1 | 9/2006 | Schaufele et al. | |
| 2007/0061169 A1* | 3/2007 | Lorsch .................. | G06F 19/322 705/3 |
| 2007/0075135 A1 | 4/2007 | Dettinger et al. | |
| 2008/0109370 A1 | 5/2008 | Moshir et al. | |

OTHER PUBLICATIONS

"Information Aggregation and Group Decisions", Sobel, University of California, San Diego; Jan. 17, 2006; Journal of Economics Literature.

* cited by examiner

*Primary Examiner* — Jason Lee
(74) *Attorney, Agent, or Firm* — Carl M. Napolitano; GrayRobinson, P.A.

(57) ABSTRACT

A system and method verify and validate a user identity for enrollment in a secure personal dataset accessing system, wherein a personal dataset includes identifiable attributes of the user. Authenticity of an asserted user identity includes electronically verified identifiable attributes to form the personal dataset. A biometric identifier is automatically captured for validating the identifiable attributes by confirming that the asserted identity matches identifiable attributes. A traceable e-audit trail is provided in an enterprise infrastructure and bench mark performance indicator. A generated digital security element results in the user electronically receiving a password and unique electronic address assigned to the user. The digital security element is then transmitted to the user and enables electronic access to the personal dataset, the personal dataset having been authenticated through the verification and validation. The user can use a smartphone, tablet, PC or laptop to generate their Emergency Medical and Contact DataSet.

1 Claim, 18 Drawing Sheets

FIG. 6

PVID Privacy Class Matrix

| Privacy Levels | Class Name | Temporary | Test | General | Psychiatry | Cancer | HIV | Research | Genetics | Organ Registry | Transplant History | Employer | HIE Participation | Authorizations | Privacy Security Access/Class Definitions |
|---|---|---|---|---|---|---|---|---|---|---|---|---|---|---|---|
| Share all Data | | | | | | | | | | | | | | | |
| Restricted data sharing | | | | | | | | | | | | | | | |
| Sharing with restricted access | | | | | | | | | | | | | | | |
| No sharing of data | | | | | | | | | | | | | | | |
| Emergency Only | | | | | | | | | | | | | | | |
| Consents | | | | | | | | | | | | | | | |
| Preferences Authorizations | | | | | | | | | | | | | | | |
| Directives DNR, organ donation | | | | | | | | | | | | | | | |
| Opt-in - Opt-out | | | | | | | | | | | | | | | |
| Medical - Power of Attorney | | | | | | | | | | | | | | | |

FIG. 6A

ATTRIBUTE GROUPS:
- A: Legal name with limited demographic data
- B: Opt-Out of No data sharing except column a-f AL
- C: Share Emergency Medical & Contact Data
- D: Opt-in share my PHI with Medical Network
- E: Understand PHI will be e-encrypted & shared via HIE's
- F: Will use the following devices to create-share-receive PHI
- G: Attribute aggregation function

| FUNCTION | # | A | B | C | D | E | F | G |
|---|---|---|---|---|---|---|---|---|
| Consent | 1 | Y (default) | Y N | Y N | Y N | Y N | Personal Computer | I understand attributes can be bundled to enhance efficiencies in sharing and distributing my Protected Health Information |
|  | 2 |  |  | Break the Glass |  |  | Tablet |  |
|  | 3 |  |  |  |  |  | iPad |  |
| Understand | 4 |  |  | Y N |  |  | SmartPhone | ☐ I agree |
|  | 5 |  |  |  |  |  | cell phone |  |
| Restricted Data Sharing | 6 |  |  | Y N | Y N |  | medical device(s) |  |
|  | 7 |  |  |  |  |  | other mobile devices |  |
| Restricted Access | 8 |  |  | Y N | Y N |  | I consent that the selected device(s) will be used by me in manageing my health activities or by an entrusted 3rd party with a digital ID and LoA equal to or greater than mine. |  |
|  | 9 |  |  |  |  |  |  |  |
| Sharing with Restricted Access | 10 |  |  |  | Y N |  |  |  |
|  | 11 |  |  |  |  |  |  |  |
|  | 12 |  |  |  |  |  |  |  |
|  | 13 |  |  |  |  |  |  |  |
|  | 14 |  |  |  |  |  |  |  |
|  | 15 |  |  |  |  |  |  |  |
|  | 16 |  |  |  |  |  |  |  |
| Consent | 17 |  |  |  |  | Y N |  |  |

FIG. 6C

Emergency Medical Data Set* for

Name: Octivia Helios  Gender: Female  EMPI: NA
Authenticated* Primary HIE/RHIO: Orlando, FL FLCF32802-115
Confidential

Personal Data - Contact Information

DOB: January 22, 1945
Race/Ethnicity: Hispanic American
Primary Language: Spanish
Home Address: 123 Bastile Dr. Apt. 3
Boston, MA 02102
Phone number: home 999-999-9999
cell: 111 111-1111

Emergency Contact Data:
Physician contacts:
Dr. Thomas E. Duitrite - Primary Care
office # 999-999-9999
Dr. Julie P. Quantos OBGYN
office # 999-999-9999
Family/Friend contacts:
Hector Helios Husband 111-111-1111
Juanita Rodrigus Friend 111-111-1111

Dependent family members under 18:
Juan Hulios-son 17 - chronic;
Sally Helios-daughter - 15 w/disability
Billy Ann Helios-son - 9
Juanita Helios-daughter - 3

Local ER or Trauma Center:
Name Santa Clara General Hospital
Phone# 888-888-8888

Driver License # 7221-449-331AX
State: Florida
Vehicles registered in: Georgia
Vehicle #1 License Plate # 887 A67A
VIN # A227 9999 3333 2222 - ACA
Vehicle #2 License Plate # 257 4768
VIN # TRC3 7777 9999 8888 1111

Insurance Coverage:
Blue Cross Blue Shield of California
Plan Name: Options for Good Blue Health
Policy# XRGH12131456577
Group# BA11398
Contact# 1-877 999-1234

*Individual voluntarily consented to an Opt-in
Preference to share this Emergency Medical Data
generated from their Personal Health Record on
04/25/2009 11:11PM PDT

Emergency Medical Data

BLOOD TYPE: AB+

ALLERGIES: as of 12/03/2009
Latex - severe
Sulfa - severe
Peanuts - mild
Feline Dander -moderate

PROBLEM LIST as of 3/11/2009
Hemoptysis,
Mitral Valve Replacement,
Congenital Subaortic Membrane,
Chronic Atrial Fibrillation,
Diabetes Mellitus Type 2,
Stroke without residual deficit,
Congestive Heart Failure, Sciatia

Active MEDICATIONS as of 3/11/2009
Spironolactone (Aldactone),
Amoxicillin (Amoxicillin),
Warfarin (Coumadin),
Digoxin (Digitek),
Valsartan (Diovan),
Ferous gluconate (Ferrous Gluconate),
GlyBURIDE (GlyBURIDE),
Furosemide (Lasix),
Metformin (Metformin Hydrochloride),
Acetaminophenhydrocodone (Vicodin)

ADVANCE DIRECTIVES as of 4/25/2009
DNR and Living Will on file at Attorney's office
Medical Surrogate is named Hector Helios
Organ donation directive on file at State james amigo
Digitally signed by james amigo
DN: cn=james amigo, o=TNT,
ou=223, email=goto@home, c=US
Date: 2010.02.01 07:53:17-05'00'

Confidential - Emergency Medical Data and Contact Information - Confidential
Copyright Good Health Network, Inc. 2009

FIG. 8

IDENTITY VALIDATION AND VERIFICATION SYSTEM AND ASSOCIATED METHODS

CROSS-REFERENCE TO RELATED APPLICATIONS

This application is a Continuation-In-Part application of and claims the benefit of pending U.S. Utility application Ser. No. 13/898,669, filed May 21, 2013, which itself claims the benefit of U.S. Utility application Ser. No. 12/792,980, filed Jun. 3, 2010, and issuing as U.S. Pat. No. 8,464,046, which itself claims priority to Provisional Patent Application Ser. No. 61/183,600, filed Jun. 3, 2009, the disclosures of which are herein incorporated by reference in their entirety, and all commonly owned.

FIELD OF THE INVENTION

The present invention relates to secure data access systems, and more particularly, to such data access systems that operate under emergency conditions such as needed in medical service environments.

BACKGROUND

The Health Insurance Portability and Accountability Act of 1996 (HIPAA), the fundamental privacy principles of both the Data Protection Act and the Human Rights Act 1998, along with the American Recovery and Reinvestment Act (ARRA) in February 2009 and Accountable Care Act (ACA) followed by April rulings by the Federal Trade Commission (FTC) included a standard of privacy regarding an individual's right to privacy regarding health care data. In January 2013, a new revision of HIPAA 1996, labeled the HIPAA Omnibus Rule, was issued with increased emphasis on privacy, disclosure of identifiable information and tougher security provisions which comes under the 2009 HITECH Act and the Genetic Information Nondiscrimination act. Under the provisions of HIPAA, ARRA, ACA and the FTC, health information, with few exceptions, can only be shared with the express permission, advance consent, and authorization of the patient (or the patient's legal guardian, as appropriate), and when compromised, electronic notifications (transactions) must be sent, and followed up with electronic audits and risk analysis.

By way of example, if a patient is unconscious and has provided advance authorization and consent for a licensed health care provider to securely access and view health-related and protected health information with family, next-of-kin, friends, or others involved, the patient's care and emergency care can be shared when in the best interest of the patient.

In Florida, vehicle owners can securely store emergency contact information electronically, including the name and telephone number of at least one person, and link same to their driver's licenses (DL). A law enforcement officer or first responder, if they can locate a driver's license at an accident scene, can contact the Department of Motor Vehicles to obtain emergency contact (ER-Cont) data. If not available and the vehicle occupants are unconscious or otherwise unable to communicate, notifying the family can be a challenge. ER-Cont information is only available to police at a crash scene in the state of Florida.

NLETS, the National Law Enforcement Telecommunications System, part of Department of Justice, can interface with Department of Motor Vehicle sites across the country and obtain emergency contact information, but only if linked to a vehicle's vehicle identification number (VIN) and with the driver's consent. However, medical data cannot be collected, stored, accessed, or shared via NLETS, which can cause a loss of critical time gaining access to critical healthcare data, such as allergies, blood type, and other medical data. Such data can save lives or improve the quality of life after a life-threatening event. In addition the Government, in 2013, added the Federal 'First Net' a telecommunication secure spectrum for Emergency Responders, part of the Department of Commerce.

As will be addressed throughout this disclosure, attributes contain information about a subject (known also as an actor). A subject's digital ID has a limited number of identity attributes such as address, age, title or driver's license or trait features that are inherent such as eye color, gender or birth place. A subject can also have acquired associated attributes (lifestyle, purchasing behavior, medical or banking activities) which can change easily whereas trait attributes most likely do not change. Upon being validated and authenticated with a digital ID (public key certificate attributes) and or authenticated attributes in good standing, then a person's (subject) authenticated identity can be enhanced with attributes that originate from an Attribute Certification process where one's Authentication privilege is extended to provide "certified binding attributes' such as access control, secure email, access privileges and associated relationships. As a result of the security and auditing process incorporated into Attribute Certification there is a strong privilege management policy monitoring effort, risk management process and certificate-attribute revocation process. Entities, institutions, exchanges, enterprise servers and the environment (defined as 'objects') can also have attributes which are represented by defined characteristics and functions. Attribute certs cannot be used to establish an identity but are used to extend the attributes of one's identity. The forgoing is in concert with NIST guidelines.

Anonymization and Pseudonymization are specific de-identification processes that file the intent of HIPAA 1996 and the HIPAA omnibus rules of January 2013. Anonymization is the process that removes the identifying characteristics (HIPAA defined) associated with protected health/clinical information and generates a not so unique health data set. The value of such allows a subject/patient to make a part of or subset of their clinical data available for a range of secondary purposes without having to access identifiable clinical information. Such data will be made available on a need to know or on an arranged basis and risk of identity is greatly minimized. The activity is handled through a trusted third party who attests to the validity of the clinical information. Pseudonymization is a specialized class of Anonymization that removes the association and adds an association between a particular set of data characteristics relating to the data subject in addition to adding more pseudonyms. This is a means by which information can be linked together to the same group of persons over time and across multiple data records without revealing the identity of the person and subject data. A trusted third party play's a critical role if there needs to be a re-identification event that is in response to a major public health event. (Activities defined in HIPAA, ACA and HITSP-ONC).

Yet further, there is a need to provide medical help for a patient using a smartphone. By way of example, if the patient is unconscious and has provided advance authorization and consent for a licensed health care provider to securely access and view health-related and protected health information with family, next-of-kin, friends, or others involved, the patient's care and emergency care should be able to be shared when in the best interest of the patient, and in particular during a medical emergency situation where a smartphone provide time access to patient medical information.

Therefore, it would be beneficial to provide a secure system and method for making both VIN and emergency medical data available on an as-needed basis to licensed emergency medical responders, in order that care be provided in a more efficient, safe, and secure fashion if such data can be voluntarily provided and stored in a secure and separate, non-law-enforcement repository, and linked to the NLETS and the Government's 'First Net' telecommunication spectrum for Emergency Responders, both trusted secure infrastructures.

SUMMARY

A system and method are provided for establishing and administering an online secure data sharing network, in particular, for use in emergency situations wherein a patient is unconscious or otherwise unable to communicate. The network enables first responders to identify victims, reach next-of-kin, reach their medical doctor, and access emergency medical data at a crash scene or other life-threatening event, the emergency data having previously been authorized for access by the patient.

The network includes an emergency medical data registry for each person who elects to participate, by validating, authenticating their identity, and consenting to securely provide emergency medical data on themselves and, if applicable, their children and family members. Such emergency medical data can include, for example, blood type, allergies, current medications, surgeries, and emergency medical contact information. The emergency medical data can only be presented in a standards-based format and viewed by a licensed healthcare worker, such as an emergency medical technician (EMT) or emergency department staff member. The data are owned by the participant, and can only be modified or deleted by that person. A real-time audit trail is available to the participant, documenting all access events, and a qualified and licensed security professional must be able to access a specific emergency event audit trail for independent auditing purposes without having access to or the ability to view any protected health data.

Embodiments of the invention may comprise a computer implemented system or method to verify and validate a user identity for enrollment in a secure personal dataset accessing system, wherein a personal dataset is electronically received and includes identifiable attributes of the user. Using a computer, authenticity of an asserted identity of the user including the identifiable attributes is electronically verified and a personal dataset formed. Biometric identifiers of the user are automatically captured on the computer for validating the identifiable attributes. The validating includes confirming that the asserted identity matches the identifiable attributes. An e-audit trail is provided having a traceable electronic enterprise infrastructure and bench mark performance indicator. A digital security element is generated as a result of the verifying and validating process and results in the user electronically receiving a password, wherein a unique electronic address is assigned to the user. The digital security element is then transmitted to the user from the computer and enables electronic access to the personal dataset relating to the user, the personal dataset having been authenticated through the verifying and validating steps.

A system and method for adding participants and licensed professionals to the network is an important feature of the present invention, and will be discussed in detail in the following.

Another registry is established for licensed emergency healthcare providers and institutions, so that their credentials, qualifications, and access privileges can be independently verified real time via a third-party source (policy and procedures) and that such validation will enable them to access the emergency medical data registry at local, regional, or national emergency events. Among the healthcare workers and institutions who may enroll are EMTs, physicians, nurses, hospitals, trauma centers, and ambulance, EVAC and AIRVAC networks, although these are not intended as limitations.

BRIEF DESCRIPTION OF THE DRAWINGS

Embodiments of the invention are described by way of example with reference to the accompanying drawings in which:

FIG. 6 is an exemplary privacy class matrix, expanded into three relational entity attribute processes;

FIG. 6A illustrates health system infrastructure interfaces (e.g. "objects") such as infrastructure, transport, HIE, HISP, and data capture mobile devices and tools, by way of example;

FIG. 6C illustrates names actor(s)/professional titles that can view defined PHI and shared with whom for a period of time, and a PHI that cannot be viewed, wherein a privacy control matrix is illustrated that designates attributes to a representative such as a medical professional, researcher, administrative specialist for an approved attribute entity, and wherein the designated representative is prequalified (having trusted credentials) to view and access a patient's protected health information as part of the healthcare management team;

FIG. 8 is an exemplary emergency medical data set according to the teachings of the present invention digitally signed by someone with access to the entire record, by way of example;

DETAILED DESCRIPTION OF THE EMBODIMENTS

Figure 1:
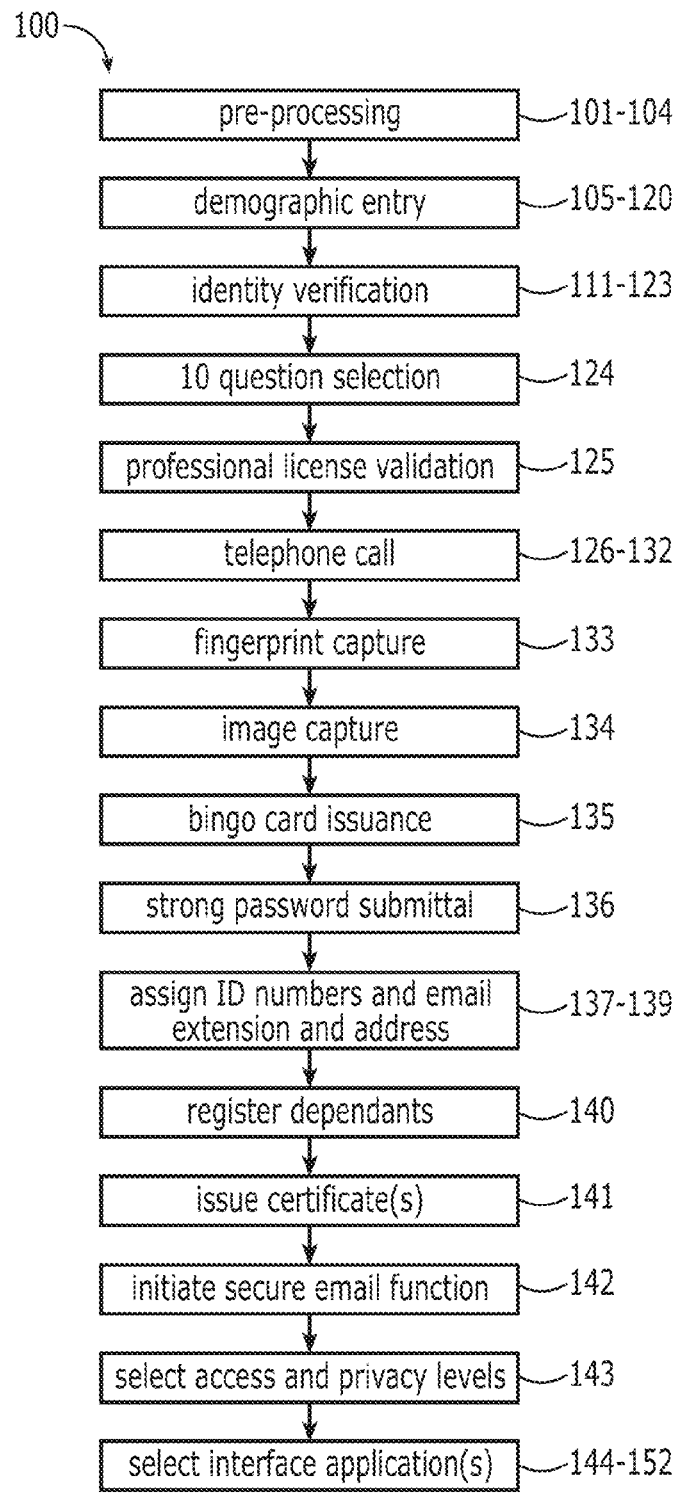
FIG. 1 is a flowchart of one process for identity verification and consent management according to the teachings of the present invention.
Figure 2A:
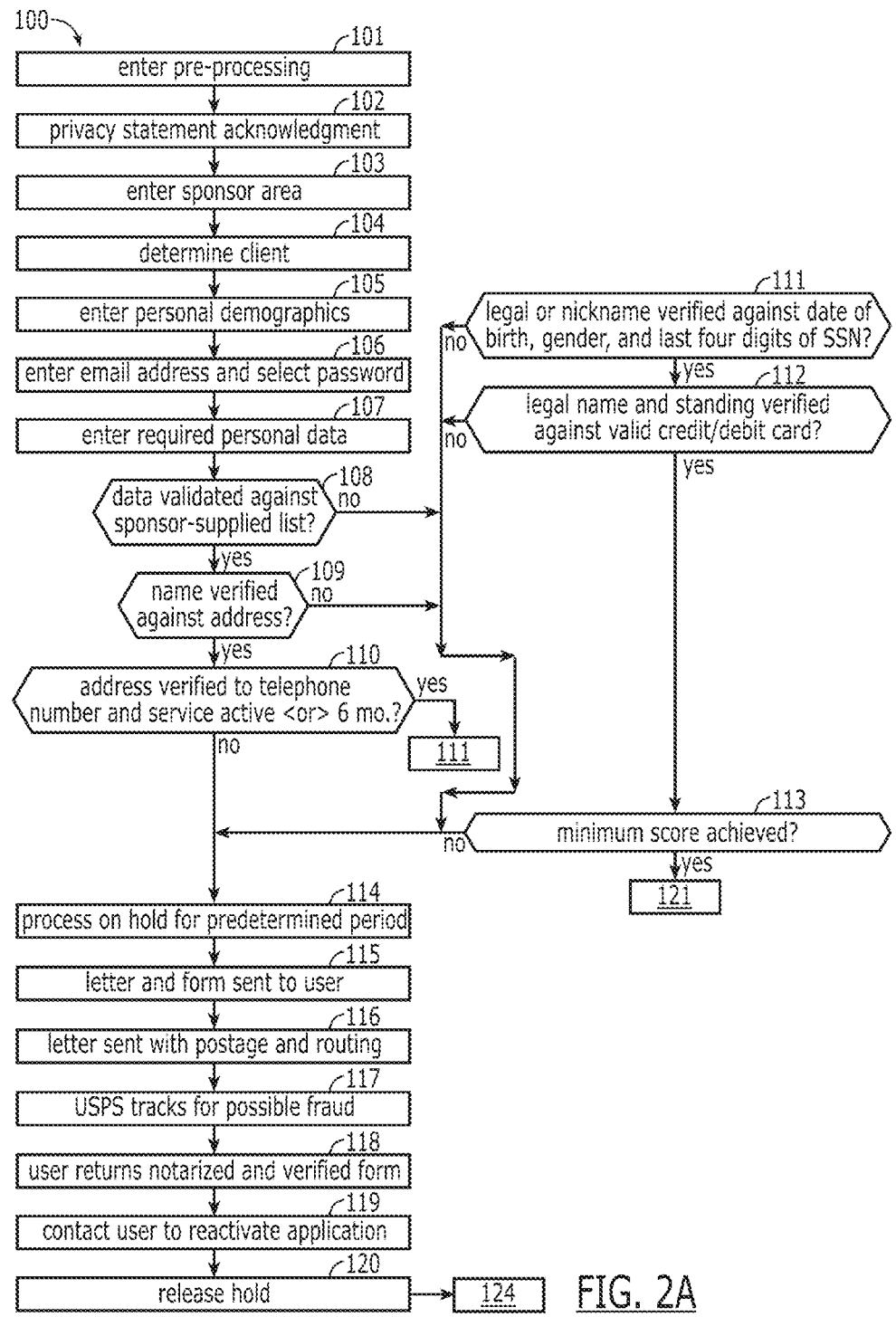
FIGS. 2A-2C are flowcharts having expanded details for the process and consent management system of FIG. 1.
Figure 2B:
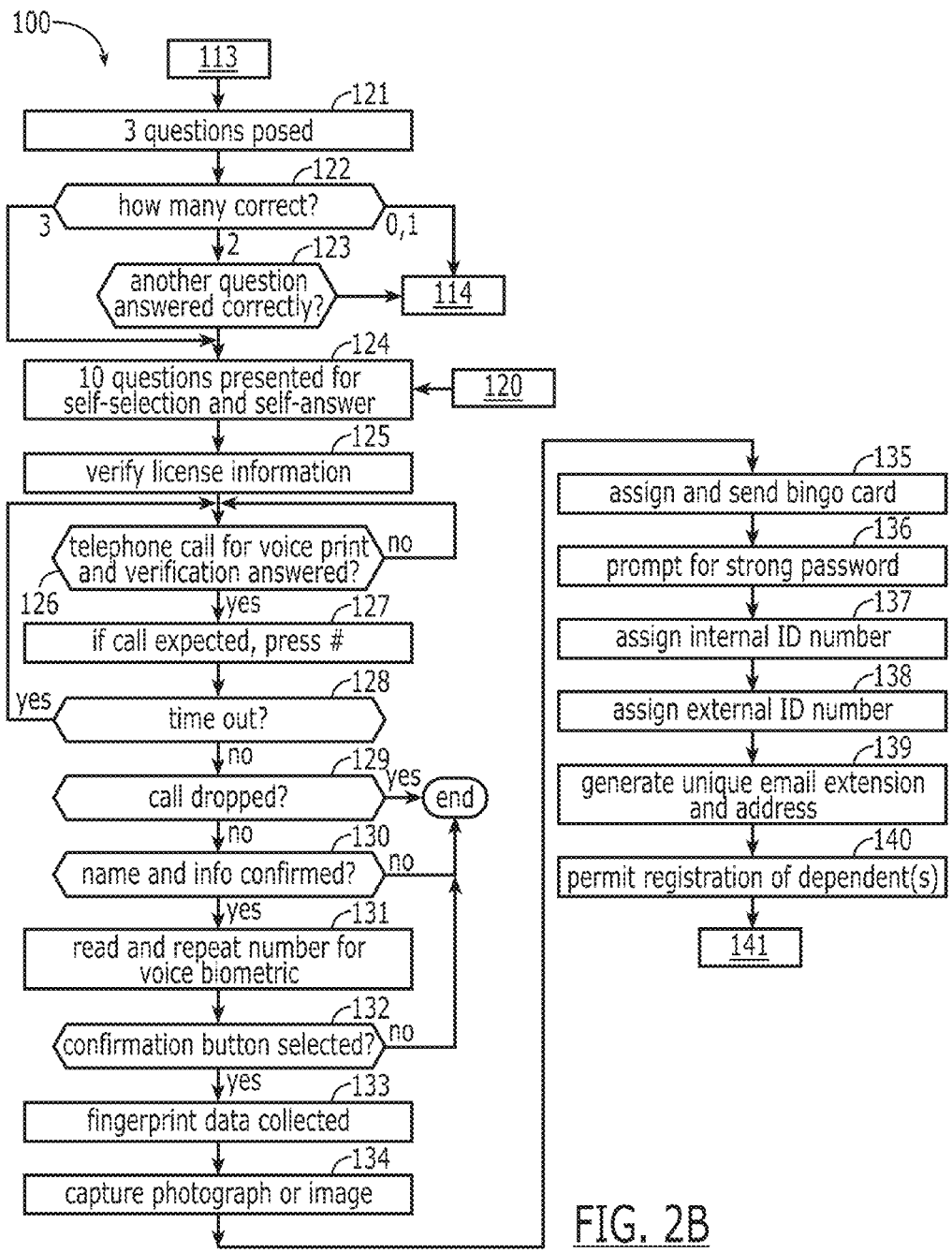
Figure 2C:
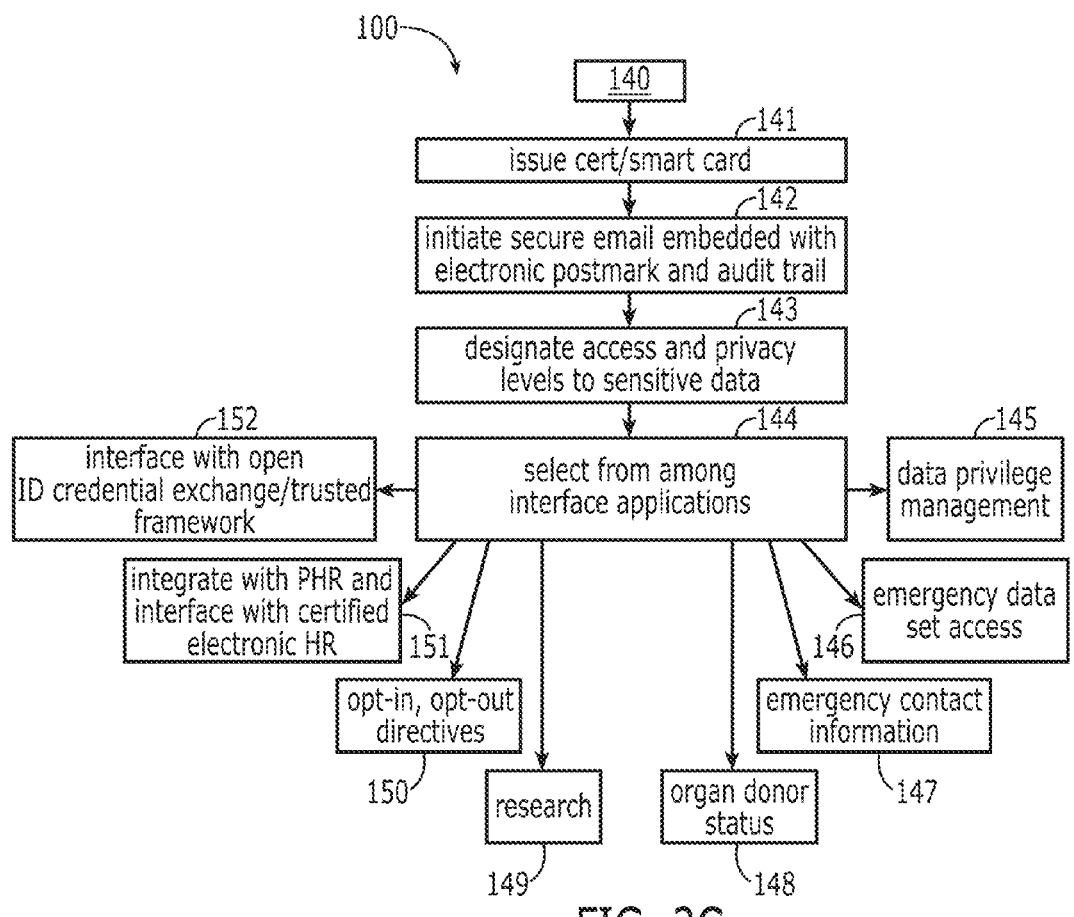

A description of embodiments will now be presented with reference to FIGS. 1A-10. An initial part of a process 100 for providing access to emergency healthcare data is directed to an enrollment process for the participant. The steps in this process 100 are outlined in the flowcharts of FIGS. 1-2C, with FIG. 1 comprising a high-level view and FIGS. 2A-2C, a more detailed view. Identity proofing is an important feature of the invention, which can have a plurality of levels depending upon the degree of assurance level desired. All levels preferably include validation of address and zip code (USPS).

A Level 1 assurance can comprise validation of a user name, with a possibly weak password being used. Level 2 can be attained with the use of a strong password and possibly a question or image definition. Assurance Level 3 requires a majority of the steps to be discussed in the following. The highest assurance level, LoA 4, would require all steps noted plus an FBI background check. There is escalating time and expense to advance through each level of assurance so in order to provide flexibility and adaptability the "Plus 1" an enhanced trust level assurance function can be added (at any level of assurance) in order to reach a preselected level of assurance that needs to be achieved. By specifying the feature and then adding one additional (Plus 1) verifying requirement there can be an increased degree of assurance so different situations can be provided by an entity's being able to select a subset of the steps of the process 100 to achieve a desired level of assurance or to achieve a desired grade level for a given class of employee, customer or executive, for example. Therefore, the invention is not intended to be limited to the totality of the steps presented herein.

An exemplary multi-step identity verification, validation and enrollment process 100 can include a preprocessing sector (block 101), which includes a user acknowledging receipt of a privacy statement acknowledgement (block 102).

The sponsor (block 103) can have, if desired, a customized front end web application for each client (block 104). Such a personalized web ID portal can include attributes by class, such as emergency data/directives and consents; financial/educational; healthcare/Rx/trials; social clubs/associations; business/professional; family/e-coupons; personal/private/governmental; and mobile and mobile-medical device registrations. One possible way of segregating the attributes is by presenting a plurality of, such as 20, pictures, from which the user selects and names one, and provides a hint word or phrase. This selection can be tested and accepted. When the next category is selected, the plurality of pictures, minus the previously selected one, is presented from which to choose.

The client can comprise, for example, an agency, association, corporation, organization, club, society, company, community of interest, group, etc. The client may or may not provide a verifiable database of qualified persons as an initial match list used to control initial access and participant correlation.

Three general classifications of clients can comprise, but are not intended to be limited to, a consumer for family enrollment, which typically will not be vetted; a company desiring only basic demographic verification, which could use a third-party trusted site, their human resources department, a patient list, or an employee list, which typically will not be vetted; and a company that desires a fully vetted process, requiring a personal identifiable verification (PIV) card and corporate verification.

The substantive part of the process 100 begins with entry of demographic data (block 105), which can include entering an email address and a selected password (for verification re-entry; block 106). All required personal data are also entered (block 107), which can include, but are not intended to be limited to, such as name, address, e-mail address, phone-cell number, citizenship, social security number, etc.

A verification request screen provides the ability to perform further validation against sponsor supplied list (block 108). Acceptance may be recognized by elements such as a government-issued ID; driver's license, Medicaid, Medicare or Food Stamp card, a PIV card, a Green Card, or a passport with a magnetic stripe that can be swiped in a reader and electronically present a matching name. In addition, or in lieu of this, an employer, membership club or organization that issues magnetic stripe card can be used as a secondary validating source.

The verification process begins by verifying the user's name to his/her address (block 109), which can comprise a third-party verification of the entered street, and then verification of the user's name to the street. This step 109 can be performed, for example, by the U.S. Postal Service (USPS), although this is not intended as a limitation.

The user's entered address is also verified against the entered telephone number (block 110). If desired, an additional set of steps can comprise validating the user's first telephone number with their carrier, and, the telephone number has been active for less than 6 months, the number can be validated to an address, with the verification of the carrier.

Next the user's name is verified against the date of birth and gender along with the last four digits of the social security number (SSN; block 111), which will typically comprise a third-party verification.

The legal name of the user and his/her standing is also verified with a valid debit or credit card via a third party, such as a national financial institution (block 112). This will typically not entail a transaction, but rather the return of just a yes or no response of good standing.

Depending upon the assurance level requested, a positive acknowledgment from steps 108-112 must be met to a minimum value (block 113). Otherwise, the process is placed on hold for a predetermined period, for example, for up to 45 days (block 114). In this case, a letter and form are electronically sent to the user (block 115), who is asked to return the letter, notarized for trust assurance levels 3 and 4, with postage and routing data (block 116). The carrier, for example, the USPS, tracks the letter for possible fraud (block 117), thereby providing third-party notarized verification. For assurance level 2, an email and letter are sent to the address provided with a unique code that when entered can reactivate a level two verification process.

The returned form letter will typically be required to be notarized, the credit/debit card verified, and mailed back to a designated address (block 118). When internally received, the form is date stamped and recorded. A message, such as an email, can be sent to the user, providing a personal access code to reactivate the application for trust level 3 or 4 assurance (block 119). The hold is then released "manually" (block 120) and the process 100 continues from block 124, joining those who had achieved the minimum score at block 113.

If the minimum score was achieved at block 113, three consumer-based questions are presented (block 121), such as, for example, third-party-providing knowledge-based questions. Depending upon the number of correct answers (block 122), the process 100 proceeds as follows.

If all three questions are answered correctly, the process continues at block 124. If only two questions are answered correctly, a fourth consumer-based question is posed (block 123), and, if this is answered correctly, the process proceeds to block 124. If either the fourth question is answered incorrectly, or only one of the three initial questions are answered correctly, the process 100 returns to block 114, wherein the process 100 is put on hold.

The process 100 for those who have satisfied the above conditions by presenting a plurality, for example, ten question options for self-selection and self-answer (block 124). The user's choices are captured and maintained.

Another aspect of the process 100 can include the verification of licensing information (block 125), such as those that the user may have acquired through training, schooling, and/or certification credits that can be issued nationally or in some other verifiable manner. Such licenses can include, but are not intended to be limited to, licenses to practice medicine, carry a fire arm, perform law enforcement duties, perform financial auditing services, carry out a professional trade, etc. These credentials can be validated, for example, via a recognized third-party credentialing service, and preferably will include an expiration date and certificate number and reflected in the attribute registry A further aspect of the process 100 includes the placement of a cell or telephone call for voice print and verification, which can comprise an out-of-bound third-party process (block 126). If there is no answer, the call can be repeated a predetermined number of times, for example, once. Preferably the user will have provided the telephone number to be used while the user is at a computer screen.

If the call is answered, the user is asked if the call was expected (block 127), in which case the user is asked to depress a telephone key, for example, the "#" symbol, to activate the telephone call part of the process. If the symbol is not pressed in a predetermined amount of time (block 128), the process ends, with a predetermined number, for example, one, repeat call, to be verified, allowable to the same telephone number. If the call is dropped (block 129), the process ends, and the user is requested to call the host, via, for example, a help desk.

If the call proceeds properly, the system repeats the user's name and confirms the entered data, and records the user's acknowledgement (block 130). Again, if there is no response, the process 100 ends. The user is asked to read and repeat the telephone number, in order to record a voice bio-metric (block 131). Then the user is asked to confirm that they provided the requested data by selecting a button (block 132). Again, if there is no response, the process 100 ends.

The process 100 continues by collecting the user's fingerprint or other biometiric (iris, palm face, ear, hand) information with the use of a third-party vendor, for example (block 133). The process 100 also includes the capture of the user's photograph and/or other type of image having a named definition (block 134). This could be provided, for example, by a third-party vendor.

The process 100 then proceeds by assigning a random "bingo card" to the user. The bingo card can be printed and transmitted to the user, for example, by a third-party vendor (block 135). As an example, a card having bar or QR code functionality and RFID could be employed that interfaces with preapproved authorized forms for consent management and privilege granting.

The user is prompted to devise a strong password for user authentication (block 136).

Next an internal unique identity number is generated and assigned (block 137) in concert with defined attributes and also a separate and distinct unique, external enterprise patient/consumer Voluntary Health ID controlled index number (VHID) is generated (block 138). The Internal role based and privacy attributes and external ID allows the consumer to manage and control privacy preferences, the sharing of restricted content such as protected health information, such as directives and emergency contact data. If a user elects to share a segment of their clinical health data for research or for the benefit of community health, they, through the anonymization function, de-identify their protected health information.

A unique email extension and address are generated (block 139) that function separately, for identity protection, and are separate and distinct from the current "user name," which is the email address used in the identity proofing process. This process can use an electronic post mark for emergency care patient tracking, incorporating the HITSP-FHIR standard and using CCR and/or C-CDA record-tracking API functions.

If desired, the user can identify and register dependents (block 140), such as minors, dependent seniors, or disabled persons under his/her full-time responsibility and direct care and who might, in an untimely accident, need to be identified and the care of whom would require access to their emergency data.

Once the user's identity has been validated via the foregoing steps, a digital certificate can be issued, for example, by a Certification Authority (block 141). Roaming certificates-attributes for fixed PC and mobile digital devices such as cell phones can be server-side based, and digital certificates, personal privacy and security attributes, can be integrated into smart ID cards or thumb drives in compliance with national NIST guidelines and FDA proposed regulations and HHS-FHIR enterprise security and trust framework infrastructure exchange regulations.

To complete the substantive validation and registration process, a secure email function is initiated that is embedded with an electronic postmark and audit trail for secure data exchange (block 142). The trusted process validates the user's ID and provides an authentication process with electronic and digital signature attribute functions (when using higher LoA's) and an e-audit function for non-repudiation. The process, which is preferably encrypted, focuses on access controls and privilege management using electronic marks integrated into each secure communication. This can apply, for example, to emergency data, a clinical trial, a financial transaction, secure document sharing, a "do not resuscitate" order (DNR), or a legal document exchange.

The user is permitted to designate levels of access to sensitive data, preferably in customized fashion (block 143). The user is asked to select a combination from among elements such as username and strong password plus one or more of the bingo card, a biometric ID, knowledge-based questions, the user's image, and digital signature, although these are not intended as limitations.

The user can also select from among at least the following interface applications (block 144) including: user preference relating to data privilege management (block 145), emergency data set access (block 146), emergency contact information (block 147), organ donor status (block 148), research (block 149), and opt-in and opt-out directives (block 150). The data can be integrated with a certified personal health record and interface with a certified electronic health record (block 151), if desired and available. The data can also interface with an open ID credential exchange/trusted framework (block 152).

Figure 3A:
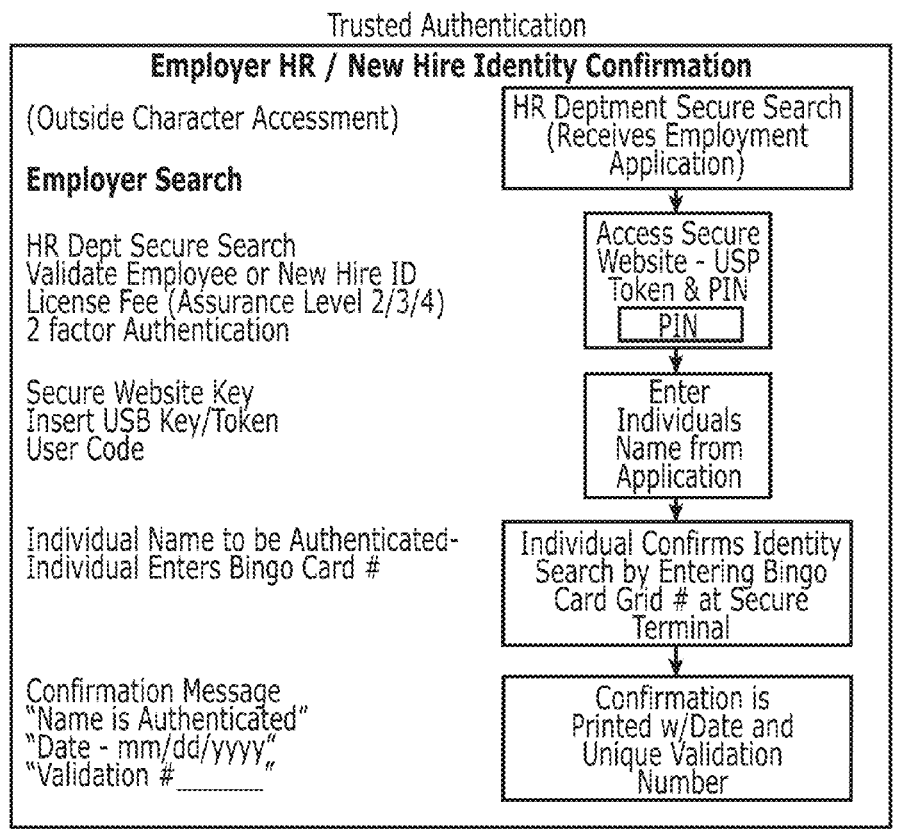
FIGS. 3A-3C are block diagrams illustrating trusted authentication, including employer/new hire identity confirmation (FIG. 3A), hospital search/emergency department (FIG. 3B), and registered first/volunteer responders (FIG. 3C)
Figure 3B:
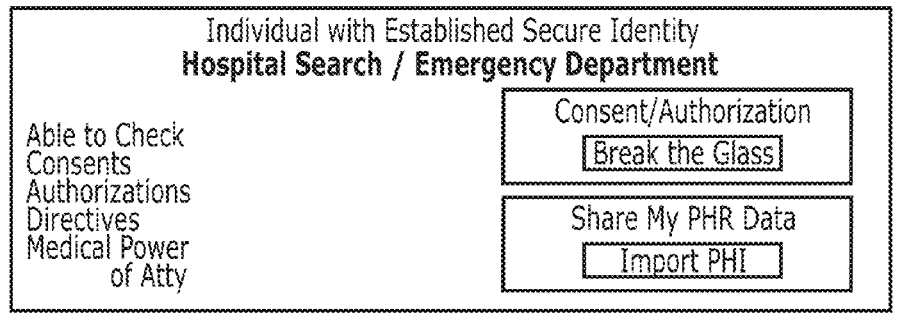
Figure 3C:
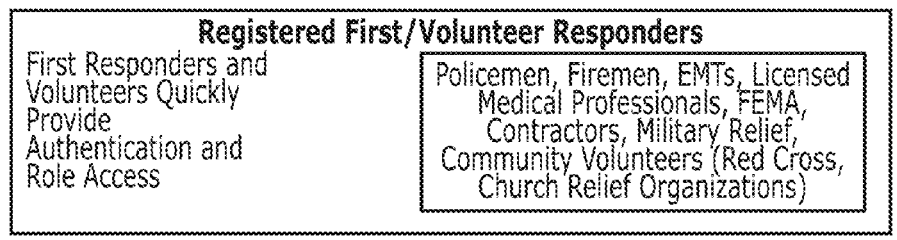

FIGS. 3A-3C illustrate the three types of trusted authentication: employer/new hire identity confirmation (FIG. 3A); hospital search/emergency department (FIG. 3B); and registered first/volunteer responders (FIG. 3C).

Figure 4:
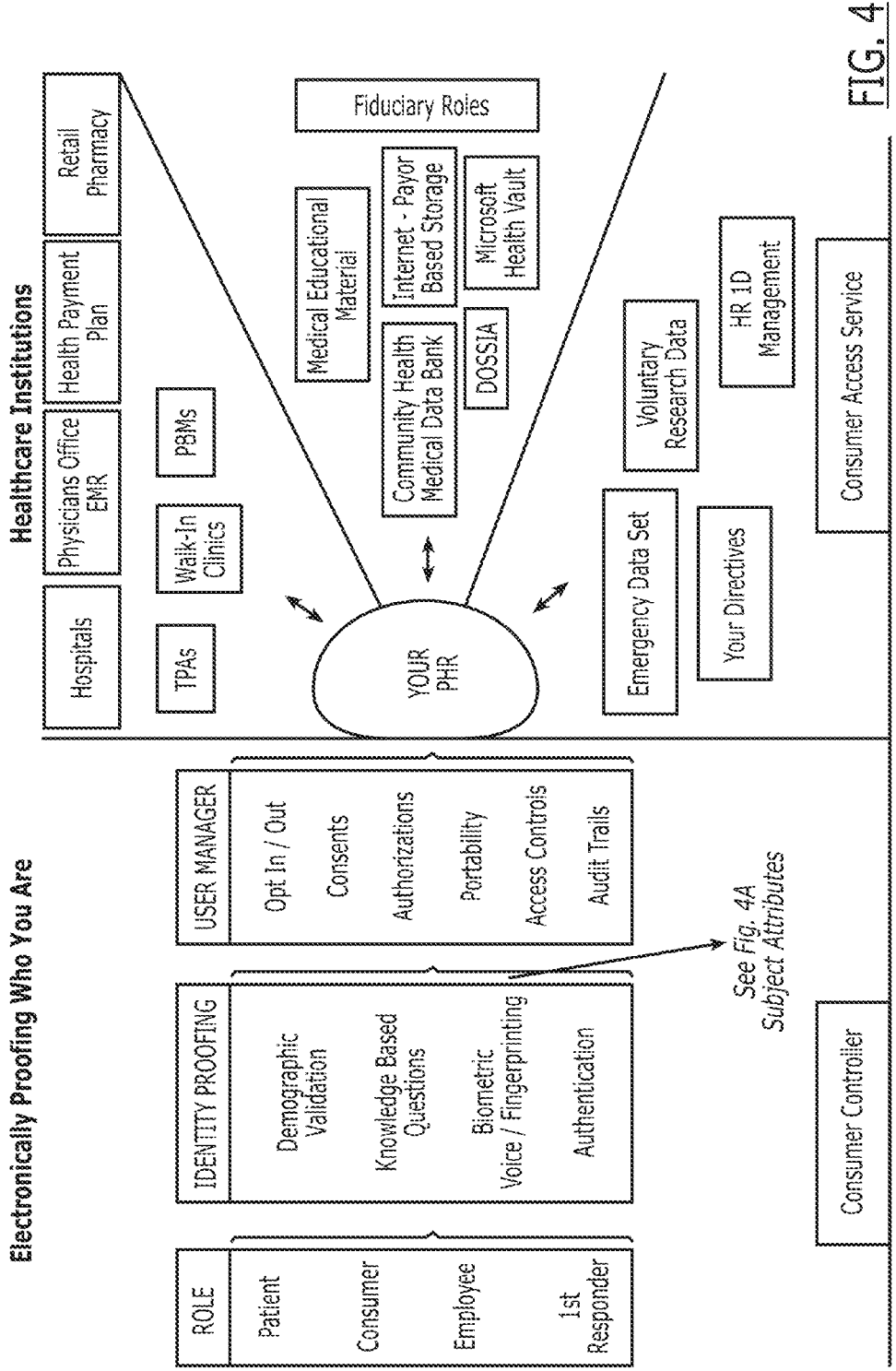
FIG. 4 is an authentication flowchart of one role-based identity proofing system illustrating an interaction of a personal health record with a healthcare institution.
Figure 4A:
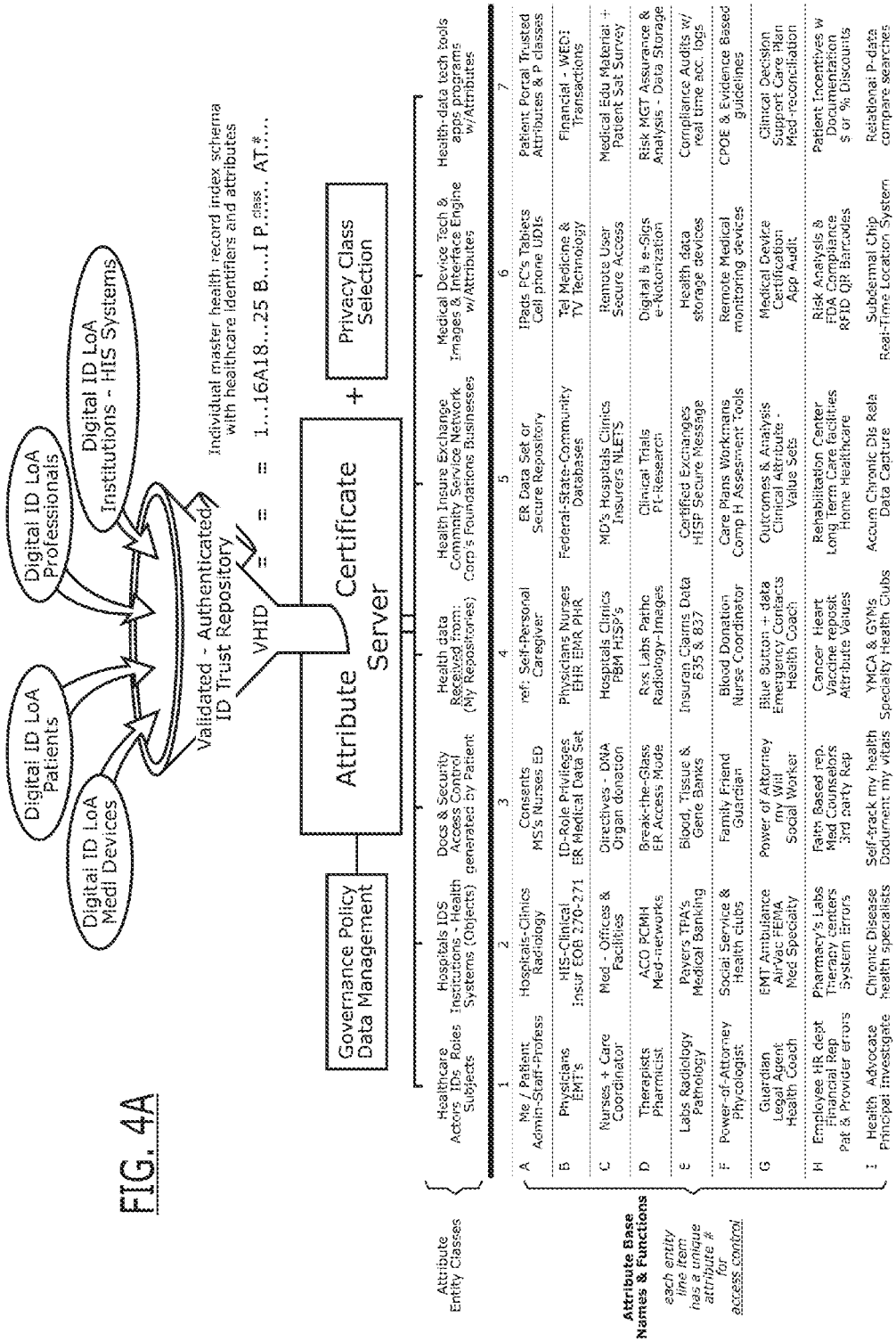
FIG. 4A is an Attribute functional matrix for one line item Role Based Access Control and Privacy Class data management illustrating a patient ID and relational entity attribute structure with designated functions for access control, by way of example.

FIG. 4 is a flowchart of role-based identity proofing and the interaction of a personal health record (PHR) in order to populate the Emergency Data Set (FIG. 8) and to make available to emergency responders and hospital emergency departments. I also provides a platform to send and receive health information for doctors and healthcare institutions. Data flow that is controlled by the consumer (left-hand side) is shown as contributing to the participant's PHR, which informs the consumer access service of the network, the ability to receive alerts, notices or copies of medical records or emergency reports from providers, a hospital or a clinic and story the PHI in their health data repository FIG. 4A provides the participant with role based and privacy attributes so they can control, share and manage their health information.

Figure 5:
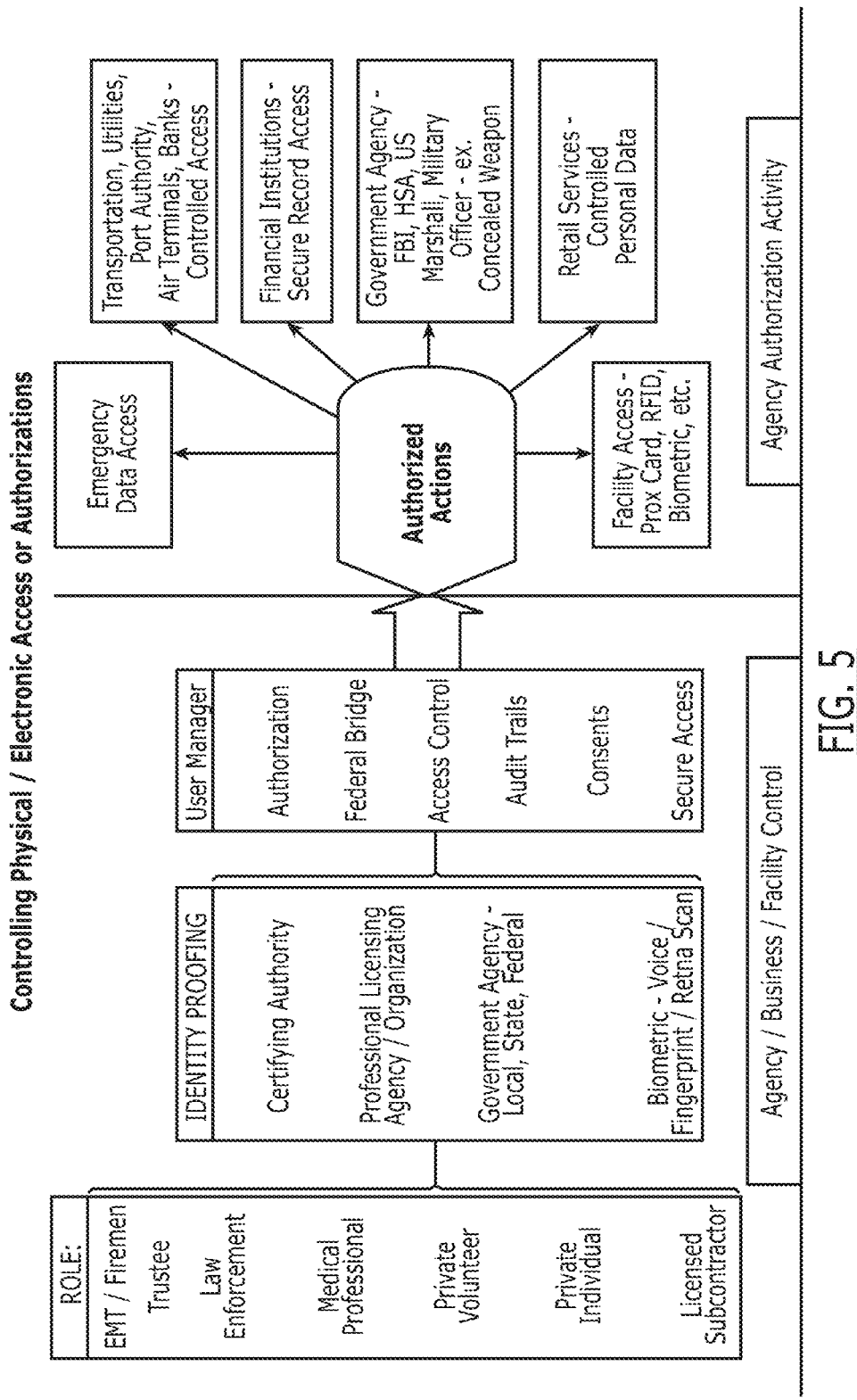
FIG. 5 is a flowchart illustrating a controlling physical/electronic access or authorizations.
Figure 5A:
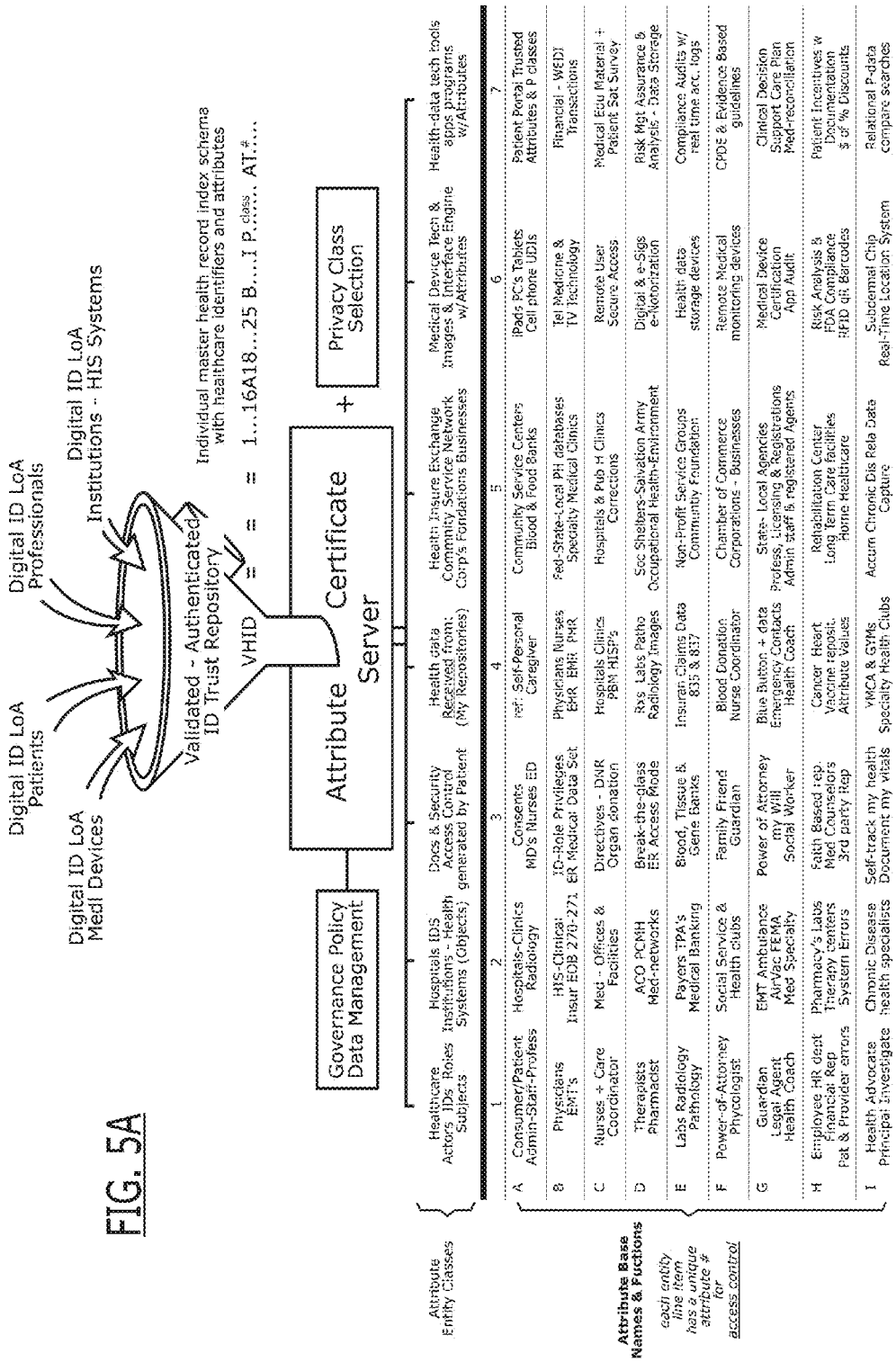
FIG. 5A illustrates one digital object ID with relational attribute structure and designated privacy and access control functions for a "health-e-community," by way of example, with a focus on registered third party entities, enterprise, organizations, human resource departments, health information service provider (HISP), identity providers, relying parties, defined repositories, associations, clubs to include government agencies, insurers, institutions and trusted authorities.

FIG. 5 is a flowchart for controlling physical/electronic access or authorizations. Here are shown the different roles of the participants, leading to their respective authorized actions and access that interface with the participant.

In use, upon the occurrence of an accident, for example, typically the police are the first to arrive and notify emergency medical services. An ambulance can be dispatched, and the police attempt to identify an unconscious/unresponsive victim. This can be attempted using the motor vehicle registration records, such as VIN#, Tag#, or DL #. The vehicle identification number is used to query a federated emergency contact registry (for example, NLETS or Federal First Net), to obtain the vehicle owner emergency contact name(s) and telephone number(s). These data are passed to the emergency responders, who can search systems for possible historic patient data.

In a particular embodiment, the VIN# registry can comprise a stand-alone system that interfaces with a state's driver's registry and interface with NLETS or First Net. An individual who registers his/her VIN# can voluntarily elect an "alert function," enabling a law enforcement office to be alerted via, for example, a red flag, that emergency medical data are available and can alert an EMT. The user can also create an emergency medical data set, using their PHR, and elect not to have a flag posted.

The emergency medical data can comprise a subset of a personal health record (PHR). These data should preferably be stored on a separate secure registry, which can only be accessed by a licensed emergency professional (e.g., EMT, nurse, fire EMT, physician, ER staff, trauma center personnel). An identifying and permission-granting technology such as a voluntary health ID (VHID) can be incorporated. As illustrated in FIG. 3C, a separate registry can be provided for licensed emergency medical professionals.

If the victim's identity is established and has consented, in advance, to use their functional and privacy attributes to make Emergency Medical Data available in case of an emergency, a membership in the network is ascertained, in which case an emergency dataset is provided to the healthcare worker. The patient can then be treated at the scene and in the hospital in a more informed manner. The NLETS and First Net data are also used to make contact with those listed in the emergency contact registry.

Consent and Privacy (HIPAA) documents can also be included in the system, such as, but not intended to be limited to, VIN# ERCont/driver's license ERCont, emergency medical dataset, "break the glass" consent/authorization, organ donation data, and DNR data.

To validate the user's demographic information at a future date, once a user is fully vetted and authenticated, a unique email address is generated that will incorporate the alpha text of their email address to the left of "@" followed by a forward slash (/) mark, at which time their validated address will be inserted excluding state and including zip code immediately followed by @. After the "@" mark will be "USPS.GOV>" (sample: jkragh/1024orangeaveorlando32802@usps.gov) encrypted. At a future date both this email (address inserted) can be sent to the USPS to validate its authenticity accompanied with an attachment of a new address of the user if such applies. This process is for authenticating and revalidating an authenticated ID or "elink authentication."

In summary, the system and methods of the present invention permit the establishment of a trusted process for interoperable identity management in a distributed healthcare enterprise. The system and methods provide ID proofing, vetting, and leveraging vetted authenticated cards/tokens usable in a distributed interoperable knowledge healthcare environment.

The key principles include ID proofing, generating new digital authenticated identity reference/tokens, or recognizing and accepting existing ones to provide contacts and directives. A trusted process incorporates functional, institutional and privacy attributes linked to participants digital ID is included for generating an enhanced token in compliance with Federal Guidelines and Regulations and established policies. Real-time authentication or verification of identity are coupled with privileges bound to role-based access controls and/or to attribute based access controls and linked to "rules-of-the-road" and "best practices" as applicable across multiple trusted domains, medical professional, and healthcare user communities to address medical emergencies and disasters. Communities and organizations define their own policies, rules, privileges, and criteria, which can be distributed. HIPAA, state, and stimulus guidelines are followed, offering a common foundation for recognizing authenticated identities in a variety of public and private healthcare settings across the national landscape, and even internationally.

Clear definitions of trusted "rules of the road" and recommended policies are provided for adoption in healthcare, and the ability to apply the rules consistently within local, enterprise, and federated architectures. This provides a cross-cutting functionality, which addresses the typically inconsistent methodologies inherent in current healthcare facilities. A foundation for privilege and attribute management is provided, which can include an expanded reach with business associate agreements, certified personal health records, and certified electronic medical records.

Further, consistent implementation is balanced with potential cost/risks. The system and methods have appropriate levels of trust/assurance, with both identity and assigned attributes. A common foundation is also provided for education and promotion, and a cost-effective process for a more common risk-management framework.

An exemplary privacy class matrix is depicted in FIGS. 6, 6A, 6B and 6C illustrating elections that can be made by the user regarding privacy levels (to share all data, restrict data sharing, share with restricted access, no sharing of data, and emergency-only sharing of data). Any number of classes can be devised for each of these privacy levels, so that a user can select a privacy level over a multitude of domains, such as a disease state.

Recognizing that not one size fits all in proving one's identity, an organization or individual will have a choice in selecting the strength and integrity of the ID proofing plan they will go through, as discussed above. Following the NIST guidelines, one can select a strong authenticated ID (FIG. 7) Plan A that requires more steps in the ID proofing process and represents a higher level of "trust" than if one elects Plan B, which represents a less rigorous level of identity proofing, resulting in a moderate level of authenticated trust and therefore requiring a fewer number of steps as in Plan A. If a lower level of a trusted ID is desired (below Plan B) and only a few steps in the identity proofing process are needed, then Plan C would be utilized. A group or an organization may also elect to have a customized program of steps (FIG. 7) that must be used to achieve a passing score to achieve a desired authentication level.

Typically, each plan will have a scoring process associated with it in order to achieve a plan-designated authentication scoring level. An individual will know steps in advance that will assist in helping one achieve a designated assurance level of trust score that can be independently validated and audited. The resulting score of an identity-proofing process then results in a pass or no-pass score.

Figure 9:
FIG. 9 is a portion of the data set (contact information) of FIG. 8, with the emergency medical data set hidden from view.

FIG. 8 is an exemplary emergency medical data set layout of the present invention digitally or electronically signed by someone with access to the entire record. FIG. 9 is a portion of the data set of FIG. 8, with the emergency medical data set hidden from view.

Figure 10:
FIG. 10 is an exemplary screen shot of an exemplary portal for generating data in a user's personal health record.

FIG. 10 is an exemplary screen shot of an exemplary portal for generating data via a user's personal health record.

By way of further example, the forgoing matrix graphics of FIGS. 4A, 5A, 6A, 6B and 6C as representing relational steps associated with a patient/actor using their Digital ID in granting access and viewing privileges to their PHI. When a cell in one of the matrixes is selected (a Column-Row alpha-numeric construct) by a patient, the cell and line item selected within the cell generates a unique algorithmic attribute (4A.c1001.a.rB001.1L200.exd_____.t). This patient centric process provides a platform for adapting to the changing landscape of technology, Federal Mandates, Guidelines and Standards while generating e-audit trails. This harmonizing sequence of linking attributes between Actors, Objects, Functions and Infrastructure patient granted Access Control functions coupled with Privacy viewing and PHI sharing privileges.

By way of further example, in case of an emergency a patient wants EMT's and Hospital Emergency Departments to have timely access both an Emergency Medical Data set and an Emergency Contact list. To achieve this goal, a consumer/patient who has been authenticated and has a Digital ID would consider providing consent on what specific information the consumer/patient wants shared with in the medical community defining specific events, titles and institutions as to what specific data is shared. In this scenario the consumer/patient starts with graphic of FIG. 4 (macro view) and FIG. 4A, a detailed view, which address how an individual engages the healthcare system in sharing emergency PHI. The patient selects cell 1B line 2 which is 'EMT's' along with 3B line 2 (ER Medical Data Set) and 4G line 2 (Emergency Contacts) and in the process a unique algorithmic attribute is initiated.

A health care community/enterprise functions a separate yet parallel set standards and guidelines for engaging and sharing PHI. They too can gain access, in emergencies, access to critical health data and in some cases, operating federal guidelines, they can 'brake-the-glass' to access PHI without violating privacy laws. FIG. 5 (macro view) and FIG. 5A a detailed process on how medical professionals and EMT's gain access (using an enhanced standards based process) to access Emergency Medical Data Sets Emergency Contact information, if available. A Healthcare Community is represented by institutions, networks, system, clinics, etc. and is referred to as Objects in the standards world and are assigned attributes also. Medical professionals are defined as actors with authenticated identities (mandate) which incorporate their professional medical task and the entity they represent. In this scenario an EMT selects the cell that defines the EMT's role as the EMT (1B line 2) along with information desired to perform their duties (emergency data and contact information): hence 3B line 2 is selected along with 4G line 2. This sets the trust infrastructure framework on what actors and their roles will be. Now protected health data is needed along with permission on how such should be shared.

Under HIPAA Privacy rules, the patient must provide consent as to what data they want to make available, to whom and under what conditions or events. By way of continued example, FIGS. 6 (macro view), 6A, 6B and 6C provide a sequential attribute process for enabling patient privacy consents in order to share confidential health information. This phase enables the sharing and viewing of PHI under patient defined events so the patient needs to be proactive in creating and selecting what information she or he wants shared from the health data repository. In the scenario, an EMT or ER physician/nurse must have a high degree of confidence in trusting the PHI being shared if it is to be used in clinical decision making. So a patient, using their digital ID, needs to create both an Emergency Data Set (FIG. 8) and or an Emergency Contact Set (FIG. 9) using their computerized Personal Health Record and electronically signing record, making it available to EMT's and Hospital ER Departments. To provide the proper consent acknowledgments in sharing Emergency Data a patient would need to select/approve from FIG. 6A, Column C (share Emergency Medical & Contact Data), Row 1 (consent: Yes), Row 4 (acknowledge privacy rule), Row 6 (check Yes, permitting Restricted Data Sharing and Row 8 (Yes to Restricted Access). Since the patient generated their own Emergency Medical Data Set they must select and registered the type electronic device that was used to create their Emergency Data Set (such as their Personal Computer). This provides an end-to-end data integrity linkage with the accompanying attributes so Emergency medical professional can trust the integrity of PHI being shared.

Figure 6B:
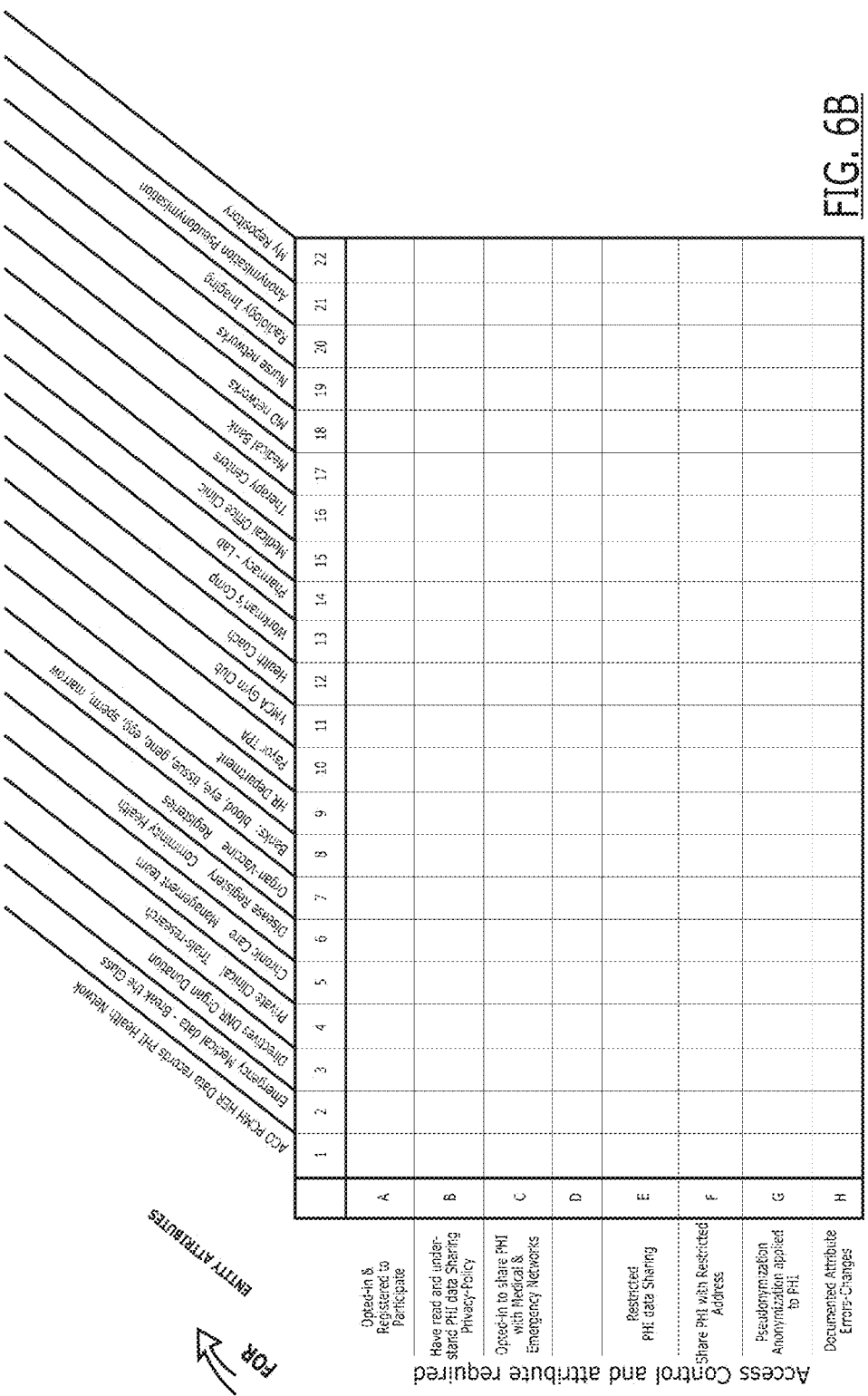
FIG. 6B illustrates parameters for sharing PHI and the entity attribute classes of Personal Health Information and defined location including by way of example, private and personal elected PHI data sharing attributes with health networks and groups including repositors, registers and designated entities.
Figure 7:
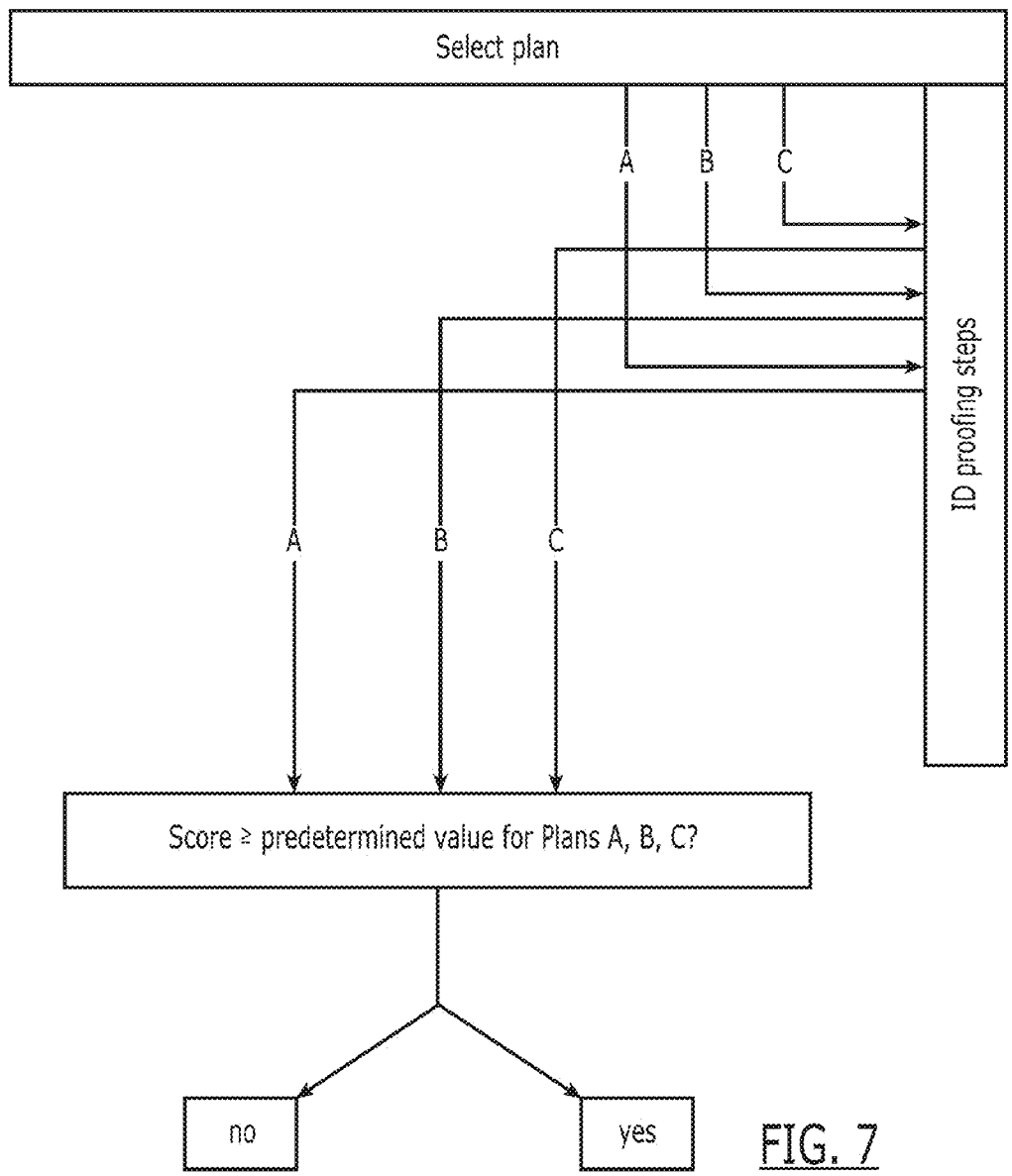
FIG. 7 diagrammatically illustrates a matrix for plan selection based upon level of authentication desired, and reflects flexibility in adopting authentication levels of assurance.

FIG. 6B links the Patient to their professional medical network or hospital system where there is an infrastructure or framework in place for sharing electronic health information and where the patient has an established relationship, agreement or contract for coordinating care and sharing PHI, specifically Emergency Medical Data. In this scenario, in FIG. 6B, Column 2 (sharing Emergency Medical Data & Break the Glass) is selected and Row A (Opt-in & have Registered), Row B (accepted PHI data sharing policy), Row C (opted-in to sharing Emergency Data), Row D (elected Restricted Access to PHI), and Row E (elected Restricted PHI Data Sharing) are checked as is 1A Electronic Health Record data allowing EHR emergency to be shared with the patient's health network.

Figure 6C:
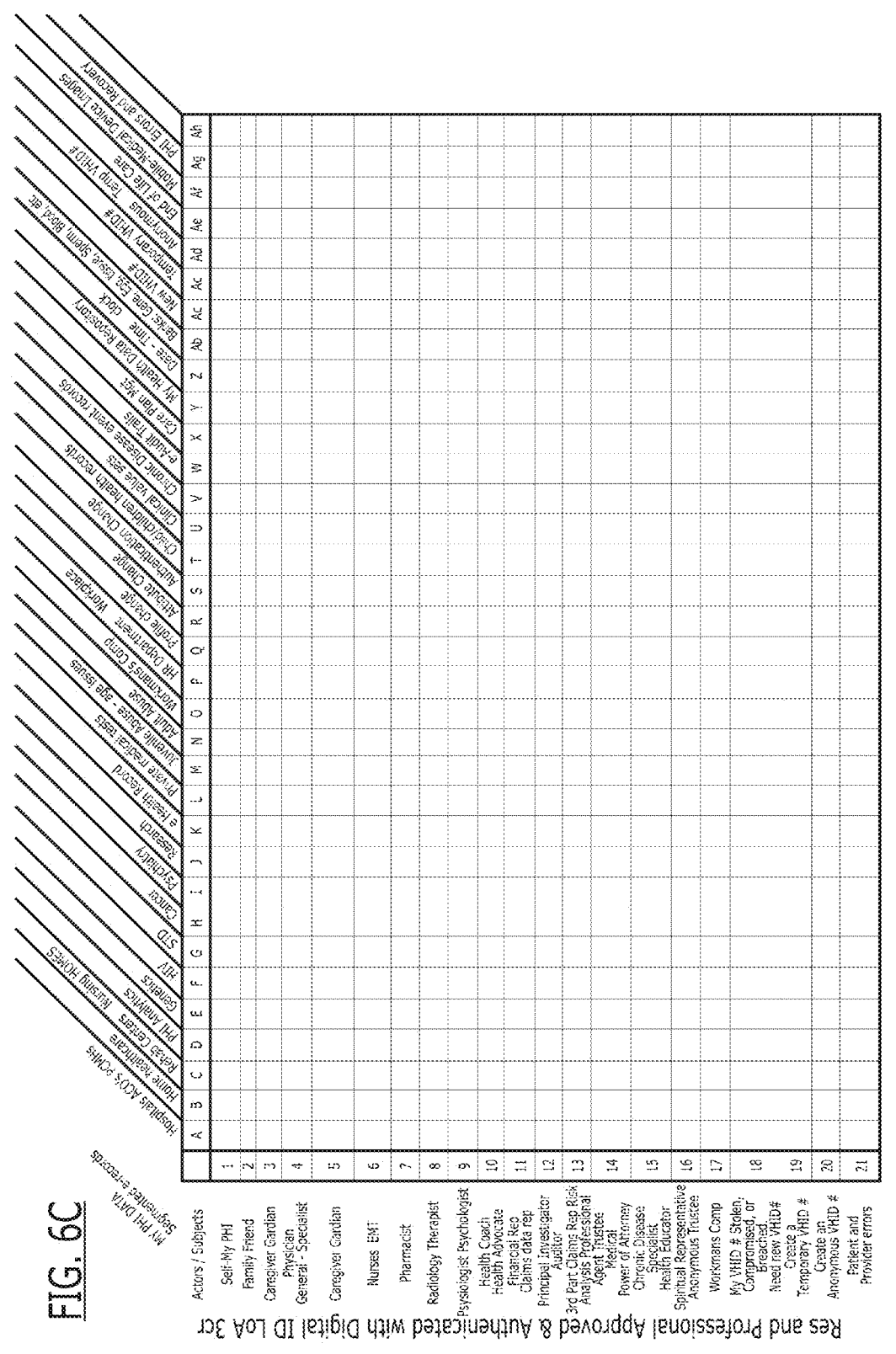

FIG. 6C specifically defines what type of protected health data can be shared and with whom, by title and or name and in what time frame if there is a defined limit. In this scenario the FIG. 6C—A6 box is checked for EMT and Hospitals, ACO's PCMH's so emergency health data is shared with them and by checking A4 the same information will be shared with the patient's personal physician. (A medical directory of names would be provided). Additionally, the patient elects to have a copy of any Emergency Medical Record placed in their "Health Data 'Trust' Repository", Y1, so it too is current. The health data repository is a patient's personal health data secure file containing their PHI and electronic copies of the EHR documents that medical providers have shared with the patient.

By way of further example, FIG. 6A-6B illustrates a voluntary digital ID privacy attribute matrix relating FIGS. 6A, 6B and 6C that collectively interface with personal privacy selections for protecting health information, by way of example, associated with features, functions and access roles assigned as per FIGS. 4A and 4B and controlled by the patient, alternatively referred to as the actor or the user.

By way of yet further example, the above described system and methods are applicable to smartphone applications including a need for emergency medical data access. The teachings of the present invention also relate to such medical data access systems that operate under emergency conditions.

Consider, by way of example, that a user has an established authenticated ID received via a recognized and standards based identity proofing, verifying and validation process, as disclosed in U.S. Pat. No. 8,464,046 for Emergency Medical Data Access System and Associated Methods, and related pending U.S. Utility application Ser. No. 13/898,669 for Identity Validation System and Associated Methods filed on May 21, 2013, the disclosures of which are herein incorporated by reference in their entireties and commonly owned. In addition, consider in addition that the user has elected, using their Authenticated ID, to populate the Emergency Medical and Contact DataSet, as described with reference to FIG. 10 that is provided with the identity proofing application.

One purpose for generating an Emergency Medical DataSet is that "in case of emergency" where the user is injured and or non-responsive, a user's Emergency Medical Information and or Emergency Contact Information (both with time-date stamped Consent's) are available for Emergency Department/EMT or Law Enforcement use. It is of interest to consider that State laws typically prohibit law enforcement from viewing a user's medical information. As a result, there are two separate and distinct presentations in a read only format, as described with reference to FIGS. 8 and 9.

The user generates the Emergency Medical and Contact DataSet using their own computerized database to populate the information and to securely post such to NLETS and First Net; secure sites. By way of example, reference is made to FIG. 2C, items 146 for emergency data set access, 147 for emergency contact information, and 148 for organ donor status, and FIG. 3B for hospital search/Emergency Department). The Emergency DataSet application, when posted, automatically "designates authenticated access and privacy levels to sensitive data" as illustrated with reference again to FIG. 2C (wherein 143 for recognizing that all licensed medical providers, including EMT's, and law enforcement are required by law (Federal and State) to have authenticated digital ID's. When the user post's their Emergency Medical and Contact DataSet to a secure site (hosted by FEMA/DHS, First Net or NLETS/Police) it is accomplished through a certified 'Trusted Framework' as illustrated with reference to FIG. 3C (item 152).

By way of further explanation and example, and acknowledging a user can use a smartphone, tablet, PC or laptop to generate their Emergency Medical and Contact DataSet, it is of interest to note that only the smartphone, is recognized by FCC, as a user registered mobile device can be used to provide access, "in-case of emergency or ICE", to "emergency contacts." Smartphones, whose attributes are bound to an authenticated user, typically have an "emergency contact icon" reflected on the initial opening screen, or may be installed, when activated which does not require an access code when used (tapped). It directly links to "in-case of emergency" (ICE) contact information screen. Law enforcement and EMTs make little use of it because data presented or a link—iconic image that requests log-on of the provider be it a qualified EMT, ER Medical Professional or law enforcement officer that when provided the Emergency Data Set would be displayed This is not done because data presented is not formally executed with a validated consent form with a time-date stamped authenticated signature or ID. Data cannot be trusted for clinical decision making.

With the teachings of the present invention, when an authenticated user (an authorized member, by way of example) integrates the defined attributes of their smartphone and related data base recognizing the smartphone/mobile device as an extension of their authenticated attributes bound to the user, the user can provide an ICE link to their personal Emergency Medical and Contact DataSet and/or have the smartphone provider provide an up link to the secure Emergency DataSet site, by way of example.

It will generally be of interest to note that one focus of the present invention is to place users in control of managing their identity and providing consent when interacting using the Internet. For a digital identity to be functional, it must be applicable in environments where a user elects to use it to be identified. Once an identity has been fully verified and validated and is authenticated, it may be converted to a digital format in various forms using identity technologies which build on each other's strength. No specific technology is singled out, only that an authenticated identity will be assigned some form of a digital certificate structure with supporting attributes. It must coexist with and complement existing authentication systems. In other words, it must be technology independent.

It may be helpful to again address use of the terms "verification" and "validation" which are independent procedures used together for checking to see that a product, service or system meets requirements, specifications and fulfill an intended propose. Verification is a process to check and determine the authenticity of an asserted identity. Validation is intended to confirm that the identity asserted matches and meets the initial attributes of the original identity and related specifications requirements such images, demographics, prints, nomenclatures and regulations. In order to strengthen the foregoing and maintain a high level of confidence in data generated and integrity in the electronic data sharing process such as in health care by way of example, the process must incorporate e-audit trails, have a traceable electronic enterprise infrastructure and generate key bench mark performance indicators.

By way of example, while Dettinger, Schaufele, and Moshir may seek to validate a resident address via the government postal service, check a state driver's license registration, a passport registration or a bank card number in order to match one piece of data to another, there is not a verifiable and true validation to a high level of confidence as to the person being who he or she claims to be. Scott T Kimmel, Biometric Technologies, Inc., the 'Event Storage' states that one needs to obtain a biometric signature and patient ID and such an event creates the foundation for generating a patient record. Yet, if the ID is stolen, then one is making an assumption that when a patient is registering that the biometric signature and the Patient ID represent an authenticated and validated ID set of attributes for that patient, thus remaking a false assumption.

Further, many states do not reciprocate and recognize another state's driver license or have ready access to passports which are under Federal control and thus lack the ability to access and check the authenticity of a passport document. State and national ID cards, financial credit/debit cards have marginal impact in verifying an identity. Biometrics data have a strong impact in the verification process when integrated with other forms of identity attributes. A biometric image captured by a government agency or a certified trusted $3^{rd}$ party, an independent party, recognized as a credentialed source is one step in fully vetting ones identity which includes verifying and validating all or as many as possible attributes of an identity. Dettinger, Schaufele and Moshir each, individually and collectively, state they would use some form of authentication (i.e. checking a driver's license) or security method (PKI) to help provide data security and assess control. If they generate the "private key" for their institution, it is self-serving for their institution thus not universal and portable as is being set forth. The three cited patent references also state they would also consider validating a digital signature which must first be vetted and established as a trusted ID attribute. Yet, in each of the three cases there is no stated recognition that the digital signature they would use would be verified independently. Hence, it would be for internal use only and not for securely sharing confidential information in a distributed enterprise. As set forth in the claimed invention, authenticity of the client/patient and verifying and validating who they are electronically generates an electronic credential, the electronic security certificate with attributes that operate via a trusted service platform.

Yet further, the references cited use of ID validating techniques within each of their closed "cloud computing" enterprises to verify their clients or customers, but the ability to transport their Intra verifiable identities' from their closed "cloud" computing system is limited if not restricted. By way of example in the world of health data automation, the process of clinical data capture and secure interoperable electronic data/file sharing of patients protected information is a centerpiece in the health exchange 'trust framework' infrastructure. The secure data exchange process only becomes a reality when each participant can be electronically identified and that occurs once their personal attributes have been fully verified and validated as to who they say they are with a high level of assurance. The claimed invention provides such a solution.

Figure 11:
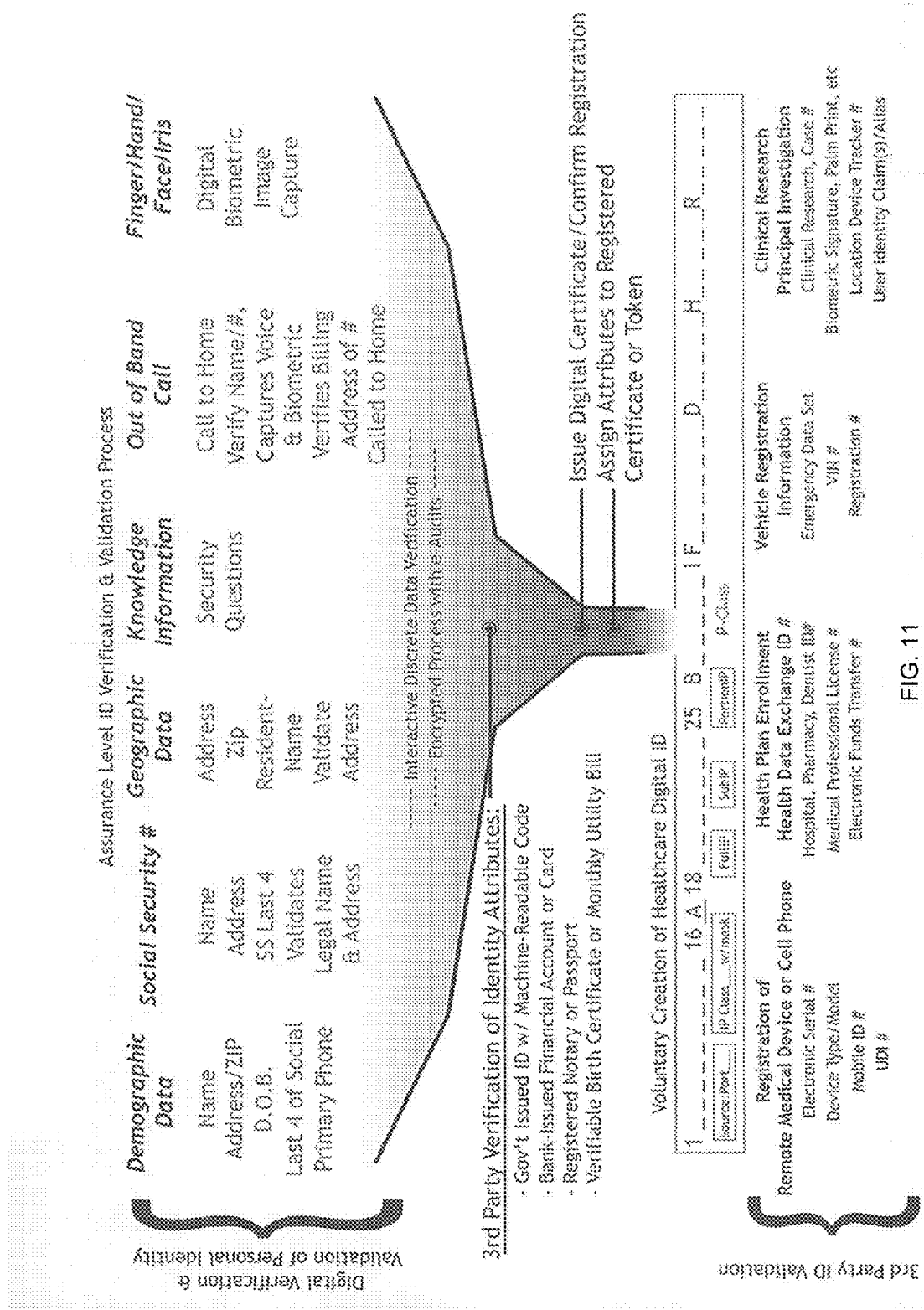
FIG. 11 is a flowchart diagrammatically illustrating the identity authentication process that may be adapted to any industry once a person is authenticated and has an authenticated digital ID.

It may also be helpful to further illustrate the assurance level identification and validation process with reference again to the flow chart of FIG. 11, by way of example, including a healthcare theme as an example for this industry has a critical identity problem. But it is important to note that the identity authentication process can be adapted to any industry for once one is authenticated and has a digital ID they can use various attributes they assign to their name/digital ID they can adopt the feature/attribute(s) they can use it to control their identity when they interact with a specific venue on the internet. Healthcare would most likely use a Voluntary/Universal ID type standards base model for identity verification while other industries would elect a different form or path such as a digital ID plus signature or voice combination that would be a site-to-user form of digital ID verification established by the business site and their customers. It is important to note that the user is in control of his identity attributes when engaging the internet and managing his content; Identity Access Management (IAM)

The flow chart of FIG. 11 runs from top to bottom and is divided into three sections with the top section including an initial phase (Digital Verification & Validation of Personal Identity) where one would have their name verified and validated using six or seven attributes of the individual in order to establish a trust level of assurance as to who that person electronically says they are. By way of example, if an assurance level is in question for the individual, then they are a candidate for further vetting or the individual may wish to achieve a higher confidence and assurance level for a trusted Identity. If such is the case, one may elect to use a 3rd Party Verification of Identity Attribute, as illustrated in the flow chart (left-center side of flow chart). Once a person's ID has been authenticated, then a Voluntary Creation of Healthcare ID is generated (with consent).

By way of further example as to how a business may use an authenticated biometric (e.g. Identity) attribute to conduct a secure transaction, consider a legally registered company with a verifiable tax ID number, address, and telephone number. Such a company may host a web site for conducting secure transactions with customers and specify that one or several authenticated biometric attributes, that have been previously verified and validated, be used to conduct and process business transactions. The ID designation includes a number that is globally unique and includes a check digit process for validating the number generated through a standards process, and then expanded to include a unique Privacy Class so that private identifiers are anonymous and may also be pseudnomious or deidentified. This provides a desirable function and distinguishing feature for a patient. For example, if one elects to add a device, a plan or other enhancing function, they must engage a third party validation process to first register the medical device or cell phone, or enroll in a health plan before such can be incorporated with their Authenticated Identity. While this process may be used when we buy a cell phone, enroll in a health plan, buy a car or engage in a research project, this activity validates the identity which has already been fully vetted (V&V).

It may be helpful to better understand the personal dataset and allowing access to at least one person other than the user by considering a Voluntary ID, by way of example as with continued reference to FIG. 11 to include four alpha-numeric categories F (families), D (an electronic Device), H (health plan), R (research or the addition of other Validated devices/features) each have numeric place holders. One purpose is to voluntarily extend one's identity to any one or a combination of a family, a medical device, a health plan, a vehicle to an organ donation plan or to a research program or the addition of a new function associated with one's identity. This transactional process provides portability of one's authenticated identity in an automated enterprise where interoperable sharing sensitive information is critical and security is mandated.

In contrast to known practices, the invention teaches completing substantive validation and registration process and reinforces the uniqueness in on-line identity proofing and an attribute authentication process. Once a person has been authenticated with a credentialed identity, the teachings of the present invention fine tune an email feature, by way of example, with additional authenticated micro object attribute features, such as presented with an electronic time-date stamped post mark which is an embedded email-authenticated object attribute, issued by the United States Post Office, by way of example. A second attribute feature reinforces the validation of a user's demographic information using an "elink authentication" process by creating a unique email address incorporating USPS.Gov as text along with the user's address, by way of further example.

Understanding terminology used by those skilled in the art will be helpful in further understanding the distinction between the claimed invention and the teachings of the cited patent references. To reiterate the above described, a person's identity has a unique authenticated identity credential with authenticated relevant personal attributes collected and recorded into the system. The individual/person is also recognized as a Subject or user and she/he can be assigned one or more attributes and object attributes. As above described, Attributes are characteristics of a subject, object or environmental condition. Attributes contain information that defines a personal identity or a name-value pair to an object. An attribute is an inherent bit of data or characteristic that can be authenticated or validated. Attributes are the key features to privacy and user access control functions. An Object Identity is a data resource that is managed by an Attribute Based Access Control system that integrates data types or groups, devices, files, records, services, tables, process, programs, applications, networks, or domains containing or receiving information. Objects are defined relationships by descriptive definitions and attributes bound to authenticated identity credentials and pre-defined operational events and environmental conditions. An Event or environmental Condition is an independent conditionally identified event or condition that is attribute identified that can be bound to a subject or objects identity and may include a current time, a day, a temperature, day-of-week, location-of-user (GPS) or an emergency event. Upon a previously defined condition or event occurring, then an Operational event will occur.

A goal of an electronic identity verification and validation process is to establish the trustworthiness of an authenticated electronic identity (eID) so that when an attribute(s) of the validated eID are presented they provide a level of confidence as to who you are electronically as a genuine person and that of an impostor. One's e-identity is a composite of verifiable evidence from that person's unique human and social elements that make up their identity. It is this uniqueness of personal attributes, features, historic actions and data elements, which when verified and validated formulate a repository of trusted attributes that generate an authenticated eID. An eID is a sensitive combination of personal attributes derived from a corroboration of evidence of one's identity comprised of unique personal elements and characteristics integrated with trustworthy personal documents that can be third party verifiable and validated. The establishment of a person's unique identity is comprised of personal identity attributes that represent: Something you are: (core and unique identifiers, a biometric, tattoo); Something you have: (birth certificate, driver's license, government issued ID/Passport, a financial account); and Something you know: (personal historic knowledge). The combination of evidence is a collection of elements with different levels of trustworthiness and authenticity. Each attribute must be validated in person, remotely via document validation signature or electronically or through a trusted third party/issuer of record with the source of such information being weighted. The combination of weighted positives and contra-indications provides a bench mark for a trust level of assurance in creating an authenticated eID.

It is important to note that no one class of attributes can provide a high level of trustworthiness to create an eID. But once a unique e-identity is created, a validated attribute of that person can be used as trusted pointer/key to person's authenticated eID. An identity verification process does not convey or grant a value, benefit or privilege. It is an electronic instrument to provide a level of authenticity and confidence as to one's eID and related trusted attributes. An authenticated eID must carry with it a high level of assurance in order to maintain trust and integrity in the eID process and to continually challenge the system to single out identities of questionable character.

A trusted identity management process incorporates critical components and national standards that generate authenticated eID's that can be trusted with a high level of assurance. The system architecture is designed around a trusted interoperable exchange of related third (relying) or independent parties focused Personal Privacy in controlling the use of one's electronic identity (eID), Security, Confidentiality, Accountability, Audiability, Traceability and Integrity. Electronic audit trails and traceability are key features that provides e-trails and electronic date stamps for measuring results and addressing claims made by others or who provided access for verification and validation activities as a trusted party or regulatory authority.

To reemphasize problems solved by embodiments of the present invention, it is again helpful to use the healthcare industry as an example. The healthcare industry, like many industries, is transitioning from a paper based system to an automated enterprise infrastructure that is electronically distributed in the medical community where personal health information and sensitive confidential data is captured electronically and securely shared. Currently licensed medical provider's (doctors, nurses, pharmacists, EMT's, etc.) who diagnose and prescribe are in the early to mid-phase in the automation process of capturing and exchanging clinical data. In late 2013, under the federal plan, patients could be incorporated into the mix, by their medical provider, empowering patients to take a more active part in managing their health activities. Patients will be engaged electronically by receiving email-reminders, text messages referencing a medical test, educational health tips and be encouraged to record and send a medical value electronically (blood pressure, blood sugar, weight, did you take medication, how do you feel today, and the like.) to their provider via their cell phone, computer or other approved medical device. The interoperable sharing of medical data is in part protected under HIPAA legislation and the accountable care act, but does not proactively offer an umbrella of protection in a litigious and fraudulent market place where identity theft and medical identity theft is on the increase. Hence a medical provider must have a high level of assurance that the integrity of medical values provided by a patient electronically is in fact from that patient, before such data can be incorporated into a clinical decision process.

Further, it will be understood by those of skill in the art that flowcharts and block diagrams herein described may illustrate architecture, functionality, and operation of possible implementations of systems, methods and computer program products according to various embodiments. Therefore, it will be understood that each block in the flowchart or block diagram may represent a module, segment, or portion of code, which comprises one or more executable computer program instructions for implementing the specified logical function or functions. Further, some implementations may include the functions in the blocks occurring out of the order as herein presented. By way of non-limiting example, two blocks shown in succession may be executed substantially concurrently, or the blocks may at times be executed in the reverse order, depending upon the functionality involved. It will also be noted that each block of the block diagrams and flowcharts, and combinations of blocks in the block diagram and flowchart illustrations, may be implemented by special purpose hardware-based systems that perform the specified functions or acts, or combinations of special purpose hardware and computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram. These computer program instructions may also be stored in a computer readable medium that may direct a computer, other programmable data processing apparatus, or other devices to function in a particular manner, such that the instructions stored in the computer readable medium produce an article of manufacture including instructions which implement the function or act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Aspects of various embodiments as herein presented, by way of example, may be embodied as a system, method or computer program product, and accordingly may take the form of a hardware embodiment, a software embodiment (including firmware, resident software, micro-code, and the like) or a combination thereof that may generally be referred to as a circuit, module or system. Furthermore, aspects of various embodiments may take the form of a computer program product embodied in one or more computer readable media having computer readable program code embodied thereon.

It is also understood that a computer implemented method as may herein be described operates with readable media relating to non-transitory media, wherein the non-transitory computer-readable media comprise all computer-readable media, with the sole exception being a transitory, propagating signal.

Any combination of one or more computer readable media may be utilized. A computer readable medium may be a computer readable signal medium or a computer readable storage medium. A computer readable storage medium may be, by way of non-limiting example, an electronic, magnetic, optical, electromagnetic, infrared, or semiconductor system, apparatus, thumb drives, or device, or any suitable combination of the foregoing that could interface with a smartphone. More specific non-limiting examples of the computer readable storage medium may include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that may contain, or store a program for use by or in connection with an instruction execution system, apparatus, or device.

A computer readable signal medium may include a propagated data signal with computer readable program code embodied therein, by way of non-limiting example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that may communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, and the like, or any suitable combination thereof. Computer program code for carrying out operations for aspects of various embodiments may be written in any combination of one or more programming languages, including an object oriented programming language such as Java, Smalltalk, C++, JASON, RestFUL API, OAUTH, Open ID2, Direct Connect or the like and conventional procedural programming languages, such as the C programming language or similar programming languages. The program code may also be written in a specialized language. The program code may execute entirely on the user's computer, partly on the user's computer, as a stand-alone software package, partly on the user's computer and partly on a remote computer, or entirely on the remote computer or server. The remote computer may be connected to the user's computer through any type of network, including a local area network (LAN) or a wide area network (WAN), certified national Data Sharing Networks that conform to the public API core architecture, or the connection may be made to an external computer, by way of non-limiting example, through the Internet using an Internet Service Provider.

Having now described the invention, the construction, the operation and use of preferred embodiments thereof, and the advantageous new and useful results obtained thereby, the new and useful constructions, and reasonable equivalents thereof obvious to those skilled in the art, are set forth in the appended claims.

That which is claimed is:

1. A computer implemented method for accessing a secure personal database using a smartphone, the method comprising:
   electronically receiving a personal dataset including identifiable attributes of a user by a hardware processor;
   electronically verifying authenticity of an asserted identity of the user including the identifiable attributes;
   electronically verifying the personal dataset;
   storing the personal dataset on the secure personal database;
   validating the identifiable attributes of the user, wherein the validating includes confirming the asserted identity matches the identifiable attributes;
   generating a digital security element as a result of the authenticity verifying and the identifiable attributes validating;
   enabling the digital security element for granting electronic access to the personal dataset on the secure personal database by an authorized member of an authorized registry;

designating privacy levels of assurance for access to the personal dataset by the user;
authorizing the access to the personal dataset by the user for the authorized member; and
activating an in-case-of-emergency (ICE) smartphone application by the authorized member.

* * * * *